United States Patent [19]
Ahn et al.

[11] Patent Number: 5,696,276
[45] Date of Patent: Dec. 9, 1997

[54] PROCESS FOR PREPARING 5,8-DIHYDROXYNAPHTHOQUINONE DERIVATIVES, NOVEL 5,8-DIHYDROXYNAPHTHOQUINONE DERIVATIVES AND THEIR USE AS ANTICANCER AGENT

[75] Inventors: Byung Zun Ahn, Youseong-ku; Kyong Up Baik, Seo-ku, both of Rep. of Korea

[73] Assignee: Kuhnil Pharmaceutical Co., Ltd., Chungnam, Rep. of Korea

[21] Appl. No.: 403,716

[22] PCT Filed: Jul. 13, 1994

[86] PCT No.: PCT/KR94/00091

§ 371 Date: Mar. 14, 1995

§ 102(e) Date: Mar. 14, 1995

[87] PCT Pub. No.: WO95/02572

PCT Pub. Date: Jan. 26, 1995

[30] Foreign Application Priority Data

Jul. 14, 1993 [KR] Rep. of Korea ............... 93-13227

[51] Int. Cl.$^6$ .................................................. C07C 50/32
[52] U.S. Cl. ............................................................. 552/298
[58] Field of Search ................................................ 552/298

[56] References Cited

PUBLICATIONS

*Chemical Abstracts* vol. 107, No. 154,149, Terada, 1987, "Synthesis of napthoquinone derivatives".
Chemical Abstract, vol. 109, No. 230484, Tanoue et al, 1988, "Synthesis of naphthoquinone derivatives".

Chemical Abstract, vol. 115, No. 145001, Torii et al, 1991, "Manf. of 5,8-dimethoxy-1,4-naphthoquinone by electrochemical oxidation".

*Primary Examiner*—C. Warren Ivy
*Assistant Examiner*—Raymond Covington
*Attorney, Agent, or Firm*—Birch, Stewart, Kolasch & Birch, LLP

[57] ABSTRACT

5,8-dihydroxynaphthoquinone derivatives represented by the following general formula (IA):

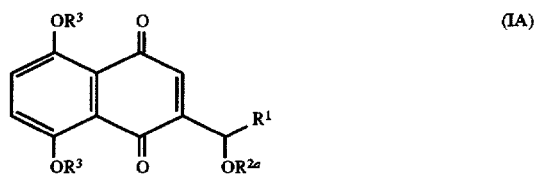

in which $R^1$ represents alkyl or alkenyl, $R^{2a}$ represents alkyl or a group —C(O)R wherein R represents alkyl, alkenyl, aryl, aralkyl or aralkenyl, which can be substituted or unsubstituted with one or more halogen(s), and $R^3$ represents hydrogen or alkyl, provided that when $R^{2a}$ is a group —C(O)R and $R^3$ is hydrogen, $R^1$ is other than 3-methyl-2-butenyl; and when $R^{2a}$ represents methyl and $R^3$ independently represents hydrogen or methyl, $R^1$ is other than 3-methylbutyl. Processes for preparing 5,8-dihydroxynaphthoquinone derivatives are also provided.

8 Claims, No Drawings

PROCESS FOR PREPARING 5,8-DIHYDROXYNAPHTHOQUINONE DERIVATIVES, NOVEL 5,8-DIHYDROXYNAPHTHOQUINONE DERIVATIVES AND THEIR USE AS ANTICANCER AGENT

TECHNICAL FIELD

The present invention relates to a process for preparing 5,8-dihydroxynaphthoquinone derivatives represented by the following general formula (I) which has an excellent anticancer activity:

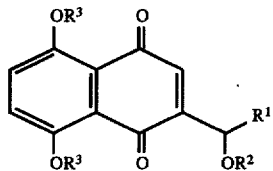

in which
R¹ represents alkyl or alkenyl,
R² represents hydrogen, alkyl or a group —C(O)R wherein R represents alkyl, alkenyl, aryl, aralkyl or aralkenyl, which can be substituted or unsubstituted with one or more halogen(s), and
R³ represents hydrogen or alkyl.

The present invention also relates to a 5,8-dihydroxynaphthoquinone derivative represented by the following general formula (IA), which is considered as the novel compound among the compounds of formula (I) above:

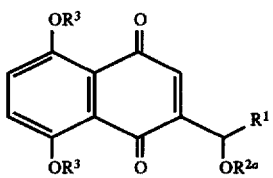

in which
R¹ represents alkyl or alkenyl,
R²ª represents hydrogen, alkyl or a group —C(O)R wherein R represents alkyl, alkenyl, aryl, aralkyl or aralkenyl, which can be substituted or unsubstituted with one or more halogen(s), and
R³ represents hydrogen or alkyl, provided that when R²ª is hydrogen or a group —C(O)R and R³ is hydrogen, R¹ is other than 3-methyl-2-butenyl; and when R²ª and R³ independently of one another represent hydrogen or methyl, R¹ is other than 3-methylbutyl.

In addition, the present invention relates to use of the novel 5,8-dihydroxynaphthoquinone derivative of formula (IA) as an anticancer agent.

BACKGROUND ART

Study of the method for treatment of cancer as one of incurable diseases of today has been actively conducted by means of chemotherapy, physical therapy and genetic engineering technique, together with study of the mechanism of attack and progress of cancer. As one of various therapeutic methods for treating cancer as mentioned above, chemotherapy attempts to treat cancer using anticancer agent. However, none of currently used anticancer agents has a satisfactory potent anticancer activity. Accordingly, attempts have been continuously made to develope an anticancer agent having a new mechanism of action and a potent anticancer activity. Such attempt to develope an anticancer agent has extended to search for substances having anticancer activity in the field of organic chemical synthesis and natural substances and further to synthesize a pharmacologically active substance from derivatives produced by transforming the component isolated from the natural product with organic chemical techniques.

As one of the progress of a series of such study, shikonin having the following formula (A) and its derivatives were proposed:

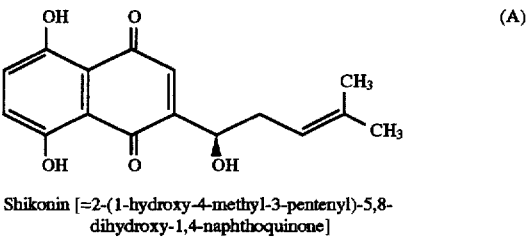

Shikonin [=2-(1-hydroxy-4-methyl-3-pentenyl)-5,8-dihydroxy-1,4-naphthoquinone]

Shikonin was first isolated from *Alkana tinctoria* by H. Brockmann in 1936 [Ann. Chem. 521, 1–47(1936)] and then from various plants belonging to Borraginaceae, and has been known as a compound having anticancer activity. However, since shikonin itself has a week anticancer activity and is difficult to absorb in the body, some derivatives wherein various substituents are introduced into a secondary alcoholic hydroxy group on 1'-position have been isolated from plants and then clinically used. Among them, typical known compounds are 1'-O-acetylshikonin [2-(1-acetoxy-4-methyl-3-pentenyl)-5,8-dihydroxy-1,4-naphthoquinone], 1'-O-isobutanoylshikonin [2-(1-isobutanoyloxy-4-methyl-3-pentenyl)-5,8-dihydroxy-1,4-naphthoquinone] and 1'-O-(3,3-dimethyl)acrylshikonin [2-(1-(3,3-dimethyl)acryloxy-4-methyl-3-pentenyl)-5,8-dihydroxy-1,4-naphthoquinone].

Thereafter, extensive study to develope shikonin derivatives has been continuously made. As a result, numerous compounds having various acyl groups introduced into the alcoholic hydroxy group of shikonin have been developed. However, for preparation of such acyl derivatives of shikonin, a method for selectively acylating only the secondary alcoholic hydroxy group among three hydroxy groups, i.e. two phenolic hydroxy groups and one alcoholic hydroxy group, present in shikonin (A) is required. Conventional methods which have been generally used for this purpose include, for example, a method for protecting the phe-nolic hydroxy group with a specific method, reacting the alcoholic hydroxy group of shikonin with acid halide and then removing the protecting group [see, German Laid-open Patent Publication No. 2831786]; a method for reacting shikonin (A) with acid halide in the presence of zeolite [see, Japanese Laid-open Patent Publication No. (sho) 61-151151]; and the like. However, such known methods have disadvantages in that they consist of multi-step procedures and therefore are complicated, and they are lacking in selectivity to produce a lot of by-product, and therefore the yield of the desired acylshikonin derivatives is considerably low.

Thus, the present inventors have extensively studied to find the method which can prepare acylshikonin derivatives in high yield. As a result, we have identified that this purpose can be established by the method according to the present invention as described hereinafter. In addition, we have supposed that other shikonin derivatives, in addition to shikonin derivatives which can be separated directly from natural product, may also have more potential anticancer activity and then prepared numerous novel derivatives (IA) having a good activity, which cannot be separated from natural products, by introducing various substituents into the side chain on 2-position of naphthoquinone nucleus. Thus, now we have completed the present invention.

DISCLOSURE OF INVENTION

Accordingly, it is an object of the present invention to provide a novel process for preparing 5,8-dihydroxynaphthoquinone derivatives having the following general formula

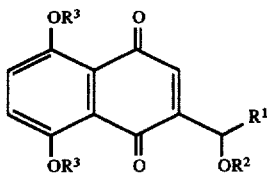

(I)

in which $R^1$ represents alkyl or alkenyl, $R^2$ represents hydrogen, alkyl or a group —C(O)R wherein R represents alkyl, alkenyl, aryl, aralkyl or aralkenyl, which can be substituted or unsubstituted with one or more halogen atom(s), and $R^3$ represents hydrogen or alkyl, characterized in that (A) a compound having the following general formula (II):

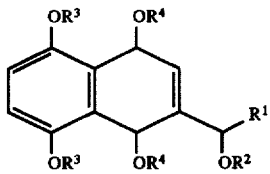

(II)

in which $R^1$, $R^2$ and $R^3$ are defined as previously described and $R^4$ represents alkyl is oxidized with cerium(IV) ammonium nitrate in a suitable solvent, or (B) a compound having the following general formula (Ia):

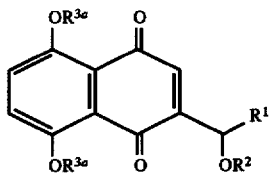

(Ia)

in which $R^1$ and $R^2$ are defined as previously described and $R^{3a}$ represents alkyl, is dealkylated to prepare a compound having the following general formula (Ib):

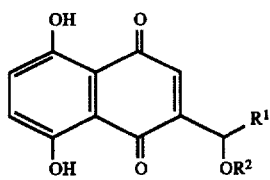

(Ib)

in which $R^1$ and $R^2$ are defined as previously described, or (C) a compound having the following general formula (Ic):

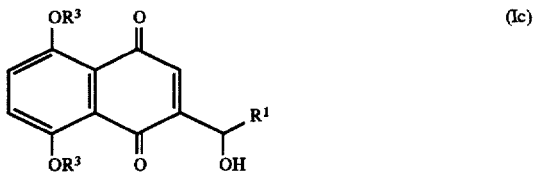

(Ic)

in which $R^1$ and $R^3$ are defined as previously described, is reacted with a compound of formula RCOOH wherein R is defined as previously described, in the presence of an organic base and dicyclohexylcarbodiimide to prepare a compound having the following general formula (Id):

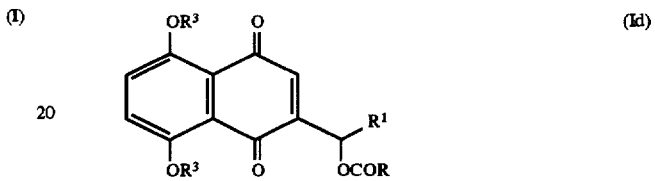

(Id)

in which $R^1$, $R^3$ and R are defined as previously described.

It is another object of the present invention to provide a novel 5,8-dihydroxynaphthoquinone derivative represented by the following general formula (IA):

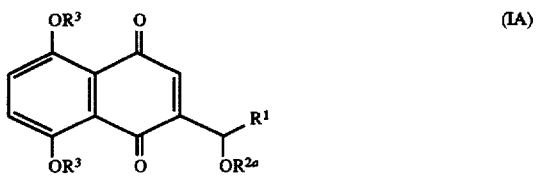

(IA)

in which $R^1$ represents alkyl or alkenyl, $R^{2a}$ represents hydrogen, alkyl or a group —C(O)R wherein R represents alkyl, alkenyl, aryl, aralkyl or aralkenyl, which can be substituted or unsubstituted with one or more halogen(s), and $R^3$ represents hydrogen or alkyl, provided that when $R^{2a}$ is hydrogen or a group —C(O)R and $R^3$ is hydrogen, $R^1$ is other than 3-methyl-2-butenyl; and when $R^{2a}$ and $R^3$ independently of one another represent hydrogen or methyl, $R^1$ is other than 3-methylbutyl.

It is a further object of the present invention to provide an anticancer agent containing a novel 5,8-dihydroxynaphthoquinone derivative of formula (IA) as defined above.

BEST MODE FOR CARRYING OUT THE INVENTION

In one aspect, the present invention relates to a novel process for preparing 5,8-dihydroxynaphthoquinone derivatives having the general formula (I) as defined above.

The process for preparing 5,8-dihydroxynaphthoquinone derivatives according to the present invention can be represented by the following methods A to C:

Method A

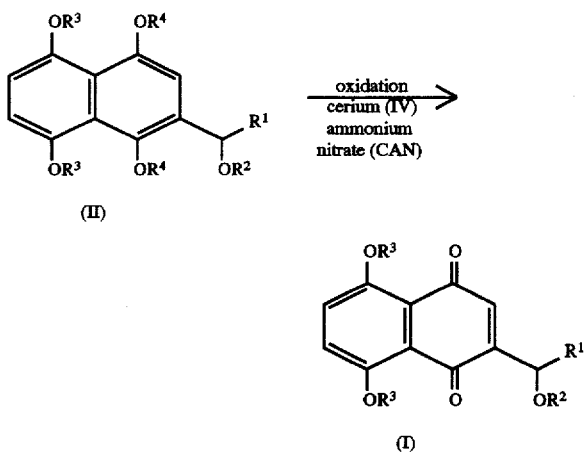

Method B

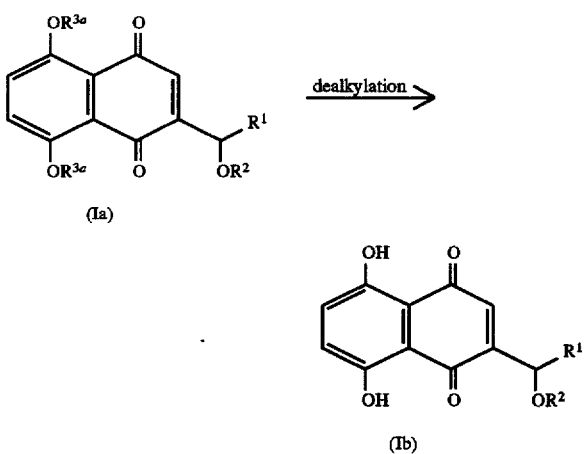

Method C

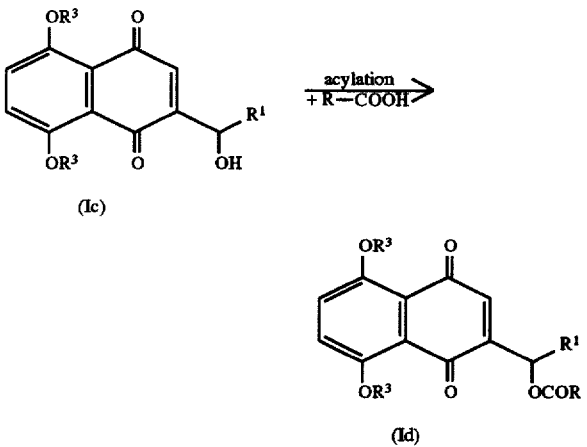

In the above reaction scheme,

R¹ represents alkyl or alkenyl,

R² represents hydrogen, alkyl or a group —C(O)R wherein R represents alkyl, alkenyl, aryl, aralkyl or aralkenyl, which can be substituted or unsubstituted with one or more halogen(s), $R^3$ represents hydrogen or alkyl, $R^{3a}$ represents alkyl, and $R^4$ represents alkyl.

In the specification of the present invention, the term "halogen" means fluoro, chloro, bromo, iodo, etc.; the term "alkyl" means a straight or branched, saturated hydrocarbon radical, preferably a radical having 1 to 20 carbon atoms, particularly having 1 to 12 carbon atoms; the term "alkenyl" means a straight or branched hydrocarbon radical containing one or more double bond(s), preferably a radical having 2 to 20 carbon atoms, particularly having 2 to 12 carbon atoms; and the term "aryl" in "aryl", "aralkyl" and "aralkenyl" preferably means a unsaturated 6-membered ring.

Hereinafter, the above Methods A to C according to the present invention will be more specifically explained.

Method A

According to the method A, the compound of formula (I) can be prepared by oxidizing a compound of formula (II) with cerium(IV) ammonium nitrate (CAN) in a suitable solvent.

The solvent which can be used in this reaction is preferably an aprotic polar solvent such as acetonitrile, dimethylformamide, etc.

In the preferred embodiment of the method A according to the present invention, first the compound of formula (II) is dissolved in the solvent and then the resulting solution is cooled, preferably to 0° to 5° C. An aqueous solution of CAN in 1 to 10 times molar amount, preferably 2 to 5 times molar amount, with respect to the compound of formula (II) is added thereto over preferably 10 minutes to 5 hours, particularly 20 minutes to one hour and the reaction solution is warmed to normal temperature and then allowed to react with stirring for several hours. When the reaction is completed, distilled water is added to the reaction mixture and the resulting product is extracted with a suitable solvent such as dichloromethane, etc., and then separated and purified by a conventional working-up procedure such as recrystallization or column chromatography.

As an example of the compound of formula (I) which can be prepared by the method A according to the present invention, the following compounds can be mentioned:

2-(1-hydroxypentyl)-5,8-dimethoxy-1,4-naphthoquinone,
2-(1-hydroxyhexyl)-5,8-dimethoxy-1,4-naphthoquinone,
2-(1-hydroxyoctyl)-5,8-dimethoxy-1,4-naphthoquinone,
2-(1-hydroxytridecyl)-5,S-dimethoxy-1,4-naphthoquinone,
2-(1-hydroxy-3-methyl-2-butenyl)-5,8-dimethoxy-1,4-naphthoquinone,
2-(1-acetoxy-4-methylpentyl)-5,8-dimethoxy-1,4-naphthoquinone,
2-(1-ethoxy-4-methylpentyl)-5,8-dimethoxy-1,4-naphthoquinone,
2-[1-(3-methylbutoxy)-4-methylpentyl]-5,8-dimethoxy-1,4-naphthoquinone,
2-(1-pentyloxy-4-methylpentyl)-5,8-dimethoxy-1,4-naphthoquinone,
2-(1-heptyloxy-4-methylpentyl)-5,8-dimethoxy-1,4-naphthoquinone, and
2-(1-dodecyloxy-4-methylpentyl)-5,8-dimethoxy-1,4-naphthoquinone.

Some of the compound of formula (II) used as a starting material in the method A above are known compounds but the other is a novel compound, which can be prepared by a method analogous to the known method for preparing the known compound of formula (II).

For example, the compound of formula (II) can be prepared (a) by reacting a compound having the following general formula (III) with magnesium halide of formula R¹MgX to obtain the compound of formula (II) wherein R² is hydrogen, i.e. a compound of formula (IIa), or (b) by alkylating the resulting compound of formula (IIa) to obtain the compound of formula (II) wherein R² is alkyl, i.e. a compound of formula (IIb), or (c) by acylating the compound of formula (IIa) with a compound of formula RCOOH to obtain the compound of formula (II) wherein R² is —C(O)R, i.e. a compound of formula (IIc). The process for preparing the compound of formula (II) of the present invention can be represented by the following reaction scheme:

Specifically, according to the preferred embodiment of the reaction (b) of the present invention, the compound of formula (IIa) and sodium hydride preferably in 1 to 10 times molar amount, particularly in 2 to 5 times molar amount, with respect to the compound (IIa) are dissolved in a suitable solvent, and then to the resulting solution are added sodium hydride and an equimolar amount of the alkylating agent. The reaction mixture is then refluxed preferably for 1 to 10 hours, particularly for 1 to 3 hours. When the reaction is completed, ice-water is added to the reaction solution, and the mixture is extracted with a solvent such as

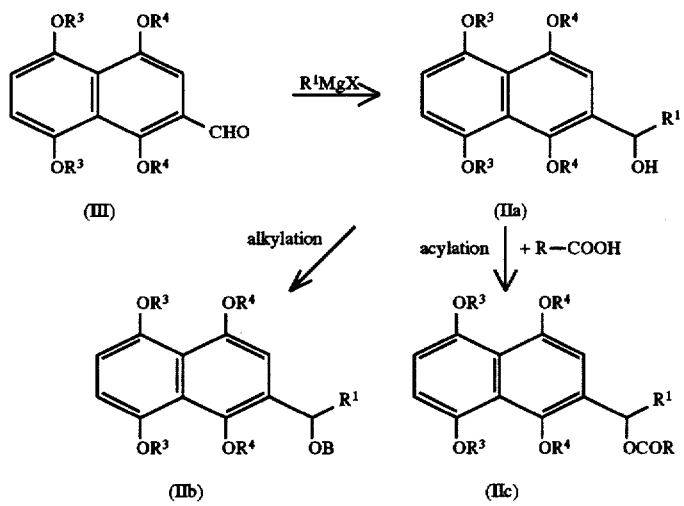

In the above reaction scheme,
R¹, R³, R⁴ and R are defined as previously described and B represents alkyl.

According to the reaction (a) above, 2-formylnaphthalene derivative of formula (III) is dissolved in an ether solvent such as dimethylether, tetrahydrofuran, etc., and then reacted by adding magnesium halide of formula R¹MgX preferably in 2 to 10 times molar amount, particularly in 2 to 5 times molar amount, with respect to the compound of formula (III). Then, the reaction mixture is treated by conventional working-up procedure. For example, saturated aqueous ammonium chloride solution is added to the reaction mixture, and the resulting product is extracted with a solvent such as dichloromethane, dried and then concentrated under reduced pressure to obtain a solid product which is then directly recrystallized or, if necessary, purified with distillation or column chromatography to obtain the desired compound of formula (IIa).

Typical examples of the compound of formula (IIa) which can be obtained by the reaction (a) above are as follows:
2-(1-hydroxypentyl)-1,4,5,8-tetramethoxynaphthalene,
2-(1-hydroxyhexyl)-1,4,5,8-tetramethoxynaphthalene,
2-(1-hydroxyoctyl)-1,4,5,8-tetramethoxynaphthalene,
2-(1-hydroxydecyl)-1,4,5,8-tetramethoxynaphthalene, and
2-(1-hydroxytridecyl)-1,4,5,8-tetramethoxynaphthalene.

In the above reaction (b) for preparing the compound of formula (II), the compound of formula (IIa) is alkylated to prepare the compound of fomrula (IIb). This reaction (b) is preferably carried out in the presence of a solvent. As a suitable solvent for this purpose, conventional aprotic solvents, for example, tetrahydrofuran, acetonitrile, etc., can be preferably used. The alkylating agent which can be used in this reaction includes a conventional alkylating agent such as alkyl iodide, alkyl bromide, dialkyl sulfate, etc., with alkyl bromide being particularly preferable.

dichloromethane, dried and then concentrated. The resulting crystalline product is treated according to the conventional working-up procedure, for example, by purifying the crystal with recrystallization from hexane and, if necessary, further purifying the product with a conventional technique, for example, distillation or column chromatography.

Typical examples of the compound of formula (IIb) which can be prepared according to the above reaction (b) are as follows:
2-(1-ethoxy-4-methylpentyl)-1,4,5,8-tetramethoxynaphthalene,
2-[1-(3-methylbutoxy)-4-methylpentyl]-1,4,5,8-tetramethoxynaphthalene,
2-(1-pentyloxy-4-methylpentyl)-1,4,5,8-tetramethoxynaphthalene,
2-(1-heptyloxy-4-methylpentyl)-1,4,5,8-tetramethoxynaphthalene, and
2-(1-dodecyloxy-4-methylpentyl)-1,4,5,8-tetramethoxynaphthalene.

According to the above reaction (c) for preparing the compound of formula (II), the compound of formula (IIa) is acylated with the compound of formula RCOOH to prepare the compound of formula (IIc).

The acylation reaction according to the reaction (c) is preferably carried out in the presence of an organic base and dicyclohexylcarbodiimide (DCC). The base which can be used for this purpose includes an amine compound, for example, dimethylamine, diethylamine, triethylamine, etc., pyridine, or dialkylamino pyridine, for example, 4-dimethylaminopyridine, etc., with 4-dimethylaminopyridine being particularly preferable. In addition, the acylation reaction can be carried out in the presence of a suitable solvent. As the solvent suitable for this purpose, optionally chlorinated hydrocarbon solvents can be used. Among them, dichloromethane, chloroform, methylene chloride, etc. can be preferably used, with dichloromethane being particularly preferable.

As typical example of the compound of formula (IIc) which can be prepared according to the reaction (c), 2-(1-acetoxy-4-methylpentyl)-1,4,5,8-tetramethoxynaphthalene can be mentioned.

Method B

According to the method B for preparing the compound of formula (I) of the present invention, the compound of formula (i) wherein $R^3$ is alkyl, i.e. the compound of formula (Ia), which can be prepared by the method A above, can be dealkylated to prepare the compound of formula (I) wherein $R^3$ is hydrogen, i.e. the compound of formula (Ib).

A dealkylating agent which can be used in this reaction can include boron tribromide, HCl-pyridine, aluminum chloride, silver oxide-nitric acid compound, etc. The particularly preferable dealkylating agent is silver oxide-nitric acid compound.

In the preferred embodiment for carrying out the method B of the present invention, the compound of formula (Ia) is dissolved in a reaction-inert organic solvent such as acetone, benzene, toluene, etc., and then to the resulting solution is added the dealkylating agent preferably in 1 to 10 times molar amount, particulalrly in 2 to 6 times molar amount, with respect to the compound of formula (Ia). The reaction mixture is then stirred preferably at 1° to 50° C., particularly at room temperature, preferably for 1 to 10 hours, particularly for 3 to 4 hours, and extracted with a suitable extracting solvent such as dichloromethane, etc. The extract is dehydrated with a drying agent, evaporated and then concentrated. If required, the resulting product can be separated and purified according to conventional working-up procedures such as recrystallization, column chromatography, and the like.

As typical example of the compound of formula (Ib) which can be prepared by the method B of the present invention the following compounds can be mentioned:
2-(1-hydroxypentyl)-5,8-dihydroxy-1,4-naphthoquinone,
2-(1-hydroxyhexyl)-5,8-dihydroxy-1,4-naphthoquinone,
2-(1-hydroxyoctyl)-5,8-dihydroxy-1,4-naphthoquinone,
2-(1-hydroxydecyl)-5,8-dihydroxy-1,4-naphthoquinone,
2-(1-hydroxytridecyl)-5,8-dihydroxy-1,4-naphthoquinone,
2-(1-acetoxy-4-methylpentyl)-5,8-dihydroxy-1,4-naphthoquinone,
2-(1-ethoxy-4-methylpentyl)-5,8-dihydroxy-1,4-naphthoquinone,
2-[1-(3-methylbutoxy)-4-methylpentyl]-5,8-dihydroxy-1,4-naphthoquinone,
2-(1-pentyloxy-4-methylpentyl)-5,8-dihydroxy-1,4-naphthoquinone,
2-(1-heptyloxy-4-methylpentyl)-5,8-dihydroxy-1,4-naphthoquinone, and
2-(1-dodecyloxy-4-methylpentyl)-5,8-dihydroxy-1,4-naphthoquinone.

Method C

According to the method C for preparing the compound of formula (I) of the present invention, the compound of formula (I) wherein $R^2$ is hydrogen, i.e. the compound of formula (Ic), which can be prepared by the method A above, can be acylated with an organic acid of formula RCOOH to prepare the compound of formula (I) wherein $R^2$ is acyl group —C(O)R, i.e. the compound of formula (Id).

The acylation reaction according to the method C is preferably carried out in the presence of an organic base and dicyclohexylcarbodiimide (DCC).

The base which can be used in the method C includes an amine compound, for example, dimethylamine, diethylamine, triethylamine, etc., pyridine, or dialkylamino pyridine, for example, 4-dimethylaminopyridine, etc., with 4-dimethylaminopyridine being particularly preferable. In addition, the acylation reaction can be carried out in the presence of a suitable solvent. As the solvent suitable for this purpose, optionally chlorinated hydrocarbon solvents can be used. Among them, dichloromethane, chloroform, carbon tetrachloride, etc. can be preferably used, with dichloromethane being particularly preferable.

In the preferred embodiment for carrying out the method C of the present invention, dicyclohexylcarbodilmide and the organic base are used in an amount of 1.0 to 2.0 mole and 0.01 to 0.5 mole, respectively, with respect to one mole of the compound of formula (Ic). In addition, the amount of the solvent used in this reaction is preferably 8 to 15 times the amount of the compound of formula (Ic). The compound (Ic) and the compound of formula RCOOH are reacted together with stirring in the presence of nitrogen gas at −5° to +5° C. for first 30 minutes and then the reaction solution is warmed to 15° to 30° C. and stirred for 1 to 3 hours. When the reaction is completed, to the reaction mixture is added n-hexane in an amount of about 100 times the amount of the compound of formula (Ic) to precipitate the insoluble material which is then filtered off. The filtrate is concentrated and then, if necessary, the synthesized product is purified by means of silica gel chromatography, gel filtration and the like.

As typical example of the compound of formula (I) which can be prepared by the method C of the present invention the following compounds can be mentioned:
2-(1-acetoxyhexyl)-5,8-dihydroxy-1,4-naphthoquinone,
2-(1-hexanoyloxyhexyl)-5,8-dihydroxy-1,4-naphthoquinone,
2-(1-octanoyloxyhexyl)-5,8-dihydroxy-1,4-naphthoquinone,
2-[1-(3-trans-hexenoyloxy)-hexyl]-5,8-dihydroxy-1,4-naphthoquinone,
2-(1-acetoxy-4-methylpentyl)-5,8-dihydroxy-1,4-naphthoquinone,
2-(1-hexanoyloxy-4-methylpentyl)-5,8-dihydroxy-1,4-naphthoquinone,
2-(1-octanoyloxy-4-methylpentyl)-5,8-dihydroxy-1,4-naphthoquinone,
2-[1-(3-trans-hexenoyloxy)-4-methylpentyl]-5,8-dihydroxy-1,4-naphthoquinone,
2-(1-acetoxyoxydecyl)-5,8-dihydroxy-1,4-naphthoquinone,
2-(1-hexanoyloxydecyl)-5,8-dihydroxy-1,4-naphthoquinone,
2-(1-octanoyloxydecyl)-5,8-dihydroxy-1,4-naphthoquinone,
2-[1-(3-trans-hexenoyloxy)-decyl]-5,8-dihydroxy-1,4-naphthoquinone,
2-(1-acetoxytridecyl)-5,8-dihydroxy-1,4-naphthoquinone,
2-(1-butanoyloxytridecyl)-5,8-dihydroxy-1,4-naphthoquinone, and
2-(1-hexanoyloxytridecyl)-5,8-dihydroxy-1,4-naphthoquinone.

The compound of formula (I) which can be prepared by the above methods A to C according to the present invention, excluding some known compounds, is a novel compound. Such novel compound is also the subject of the present invention. Accordingly, in another aspect, the present invention relates to a novel 5,8-dihydroxynaphthoquinone derivative represented by the following general formula (IA):

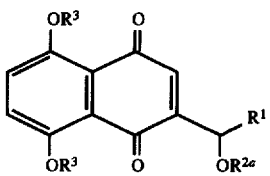

(IA)

in which

R¹ represents alkyl or alkenyl,

R²ᵃ represents hydrogen, alkyl or a group —C(O)R wherein R represents alkyl, alkenyl, aryl, aralkyl or aralkenyl, which can be substituted or unsubstituted with one or more halogen(s), and R³ represents hydrogen or alkyl, provided that when R²ᵃ is hydrogen or a group —C(O)R and R³ is hydrogen, R¹ is other than 3-methyl-2-butenyl; and when R²ᵃ and R³ independently of one another represent hydrogen or methyl, R¹ is other than 3-methylbutyl.

Among the novel compound of formula (IA) according to the present invention, the preferred compounds are those wherein R¹ represents $C_1$–$C_{15}$ alkyl or $C_2$–$C_{15}$ alkenyl, R²ᵃ represents hydrogen, $C_1$–$C_{15}$ alkyl or a group —C(O)R wherein R represents $C_1$–$C_{15}$ alkyl, $C_2$–$C_{15}$ alkenyl, phenyl, phenyl-$C_1$–$C_{15}$ alkyl or phenyl-$C_2$–$C_{15}$ alkenyl, which can be substituted or unsubstituted with one or more halogen(s), and R³ represents hydrogen or $C_1$–$C_5$ alkyl, provided that when R²ᵃ is hydrogen or a group —C(O)R and R³ is hydrogen, R¹ is other than 3-methyl-2-butenyl; and when R²ᵃ and R³ independently of one another represent hydrogen or methyl, R¹ is other than 3-methylbutyl.

As previously described, the purpose of the study of 5,8-dihydroxynaphthoquinone derivatives by the present inventors resides in development of an anticancer agent having an excellent activity. Further, anticancer activity of 5,8-dihydroxynaphthoquinone derivatives according to the present invention could be evidently demonstrated from the cytotoxicity test, and the like. Accordingly, the use of the novel 5,8-dihydroxynaphthoquinone derivative of formula (IA) above as an anticancer agent is also included within the scope of the present invention.

Cancer as one of current typical incurable diseases is difficult to completely cure because the kind of cancer and the cause of an attack of cancer are very diverse and, in most cases, the definite cancer attacking mechanism has not been established. Accordingly, numerous novel synthetic materials and natural substances have been examined for their possibility of treating cancer.

The study of anticancer activity of shikonin, which is the parent compound of 5,8-dihydroxynaphthoquinone derivative of formula (IA) according to the present invention, was conducted first by U. Sankawa [Chem. Pharm. Bull. 25, 2392–2395 (1977)]. According to this test for effect of shikonin in mouse, it has been reported that shikonin shows an increase in life span (LSI) of 92% in mouse suffering from S-180 ascitic cancer while does not show a significant effect in mouse suffering from L1210 cancer.

Meanwhile, the present inventors have identified that the ether extract of *Alkanna tinctoria* shows a potent cytotoxic activity against leukemic cell lines L1210 (Kor. J. Pharmacogn., 17, 186 (1986)). We have isolated and identified those effective components and then disclosed that one of such effective components is acetylshikonin, which has $ED_{50}$ value of 0.01 µg/ml against L1210 cells and LSI of 85% in mouse suffering from S-180 sarcoma (Kor. J. Pharm. Soc., 34, 262–266 (1990)).

According to this, the present inventors have observed a cytotoxic effect on L1210, HL-60, K562 and A549 cells and a LSI effect in mouse suffering from S-180 sarcoma, of the 5,8-dihydroxynaphthoquinone derivative of the present invention. In the cytotoxicity test, a chemotherapeutic agent, 5-fluorouracil, which has been most widely used for treating cancer in clinical field and has been recognized as having a good cytotoxicity was used as a comparative drug; and in the test for LSI effect the currently used anticancer agent, doxorubicin was used as a comparative drug. This is based on the assumption that since the structure of acylshikonin derivatives is similar to that of adriamycin which acts as an inhibitor of DNA intercalator and DNA topoisomerase type 1, the action of shikonin will be similar to that of adriamycin.

On the basis of the results from the tests for cytotoxicity and LSI effect, it could be identified that the novel 5,8-dihydroxynaphthoquinone derivative of formula (IA) according to the present invention has an excellent cytotoxicity and anticancer activity and therefore can be used as a clinically useful anticancer agent. When the compound of the present invention is used in clinical purpose, this compound can be used in the form of a suitable formulation which is conventional in the pharmaceutical field. Accordingly, the present invention also relates to a pharmaceutical composition for treating cancer which contains the novel 5,8-dihydroxynaphthoquinone derivative of formula (IA) as an active ingredient.

The pharmaceutical composition of the present invention can be prepared in a pharmaceutically conventional formulation, for example, formulations for oral administration such as tablets, capsules, troches, solutions, suspensions, and the like, injectable formulations such as injectable solution or suspension or ready-to-use injectable dry powder which can be used by reconstituting with distilled water for injection just before injection, or topically applicable formulations such as ointments, creams, solutions, and the like, using a conventional carrier according to the conventional pharmaceutical methods.

The carriers which can be used for this purpose include those conventionally used in pharmaceutical field, for example, binders, lubricants, disintegrants, excipients, solubilizing agents, dispersing agents, stabilizers, suspending agents, coloring agents, perfumes, etc., in the case of oral preparation, preservatives, painless agents, solubilizing agents, stabilizers, etc., in the case of injectable preparation, and bases, excipients, lubricants, preservatives, etc., in the case of preparation for topical use. The pharmaceutical formulation thus prepared can be administered orally or parenterally, for example, intravenously, subcutaneously, intraperitoneally, etc., or can topically apply. In addition, when the preparation is administered per oral, it can be preferably administered together with antacids or in the form of an enteric-coated formulation such as enteric-coated tablets.

Although the dosage of the 5,8-dihydroxynaphthoquinone derivative of formula (IA) according to the present invention for human is appropriately selcted depending on the absorption, inactivation and secretion of the active component in the human body, age, sex and condition of patients, kind and severity of cancer to be treated, etc., the dosage is generally in the range of 20 to 200 mg, preferably in the range of 50 to 150 mg, per a day in adult patient. However, it should be uderstood that the dosage as mentioned above can be appropriately increased or reduced using a specialized dosage regimen according to the judgement of specialists who supervise or observe the administration of drug and individual request in the case of a certain type of cancer. The effective daily dose of the active ingredient can be administered as a single dose or a multiple-divided dose, preferably over 3 to 6 times, at regular intervals.

The preparation of 5,8-dihydroxynaphthoquinone derivatives of formula (I) according to the process of the present invention will be more specifically illustrated in the following examples. However, it should be understood that the present invention will not be limited to these examples in any manner.

EXAMPLE 1

Preparation of 2-(1-acetyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 60 mg (1 mmole) of acetic acid at 0° C. under nitrogen gas, and the mixture was stirred for 30 minutes and then at room temperature for further 3 hours. 20 ml of n-hexane was added to the reaction solution. The mixture was filtered to remove the insoluble materials. The filtrate was dried and then concentrated under reduced pressure. The residue was purified with silica gel column chromatography (n-hexane: ethylacetate= 20:1–5:1) to obtain 247 mg (Yield: 75%) of the title compound having the following structure as a red precipitate.

$^1$H-NMR (CDCl$_3$, δ ppm): 12.58(s, 1H), 12.42(s, 1H), 7.18(s, 2H), 6.99(d, J=1.1 Hz, 1H), 6.00(m, 1H), 5.12(m, 1H), 2.51(m, 2H), 2.13(s, 3H), 1.69(s, 3H), 1.57(s, 3H)

$^{13}$C-NMR (CDCl$_3$, δ ppm): 178.2, 176.7, 169.7, 167.5, 167.0, 148.2, 136.1, 132.9, 132.7, 131.5, 117.7, 111.7, 111.0, 69.4, 32.8, 25.7, 21.1, 17.9

IR: 2925, 1740, 1605, 1450

MASS (rel. int.): 330(M$^+$, 2), 270(100), 255(43), 228(9), 220(71), 219(89), 163(4), 137(3), 84(47)

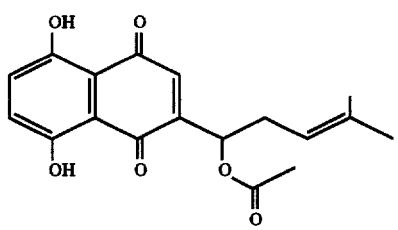

EXAMPLE 2

Preparation of 2-(1-monochloroacetyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3ml of dry dichloromethane. To the resulting solution was added 94.5 mg (1 mmole) of monochloroacetic acid at 0° C. under nitrogen gas, and the mixture was stirred for 30 minutes and then at room temperature for further 3 hours. The resulting product was separated and purified according to the procedure as described in Example 1 to obtain 218 mg (Yield: 60%) of the title compound having the following structure as a red oil.

$^1$H-NMR (CDCl$_3$, δ ppm): 12.57(s, 1H), 12.40(s, 1H), 7.17(s, 2H), 7.04(s, J=1.1 Hz), 6.07(m, 1H), 5.07(m, 1H), 4.09(s, 2H), 2.58(m, 2H), 1.65(s, 3H), 1.54(s, 3H)

$^{13}$C-NMR (CDCl$_3$, δ ppm): 176.5, 174.9, 168.8, 168.3, 166.1, 146.6, 136.6, 133.4, 133.1, 131.2, 117.1, 111.7, 111.5, 71.2, 40.6, 32.7, 25.7, 17.9

IR: 2925, 1750, 1605, 1450

MASS (rel. int.): 365(M$^+$, 3), 296(3), 271(40), 270(100), 255(46), 220(49), 219(30), 191(7), 149(10), 84(17)

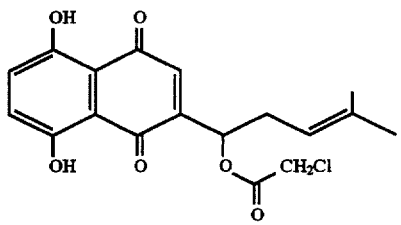

EXAMPLE 3

Preparation of 2-(1-trichloroacetyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 163 mg (1 mmole) of trichloroacetic acid at 0° C. under nitrogen gas, and the mixture was stirred for 30 minutes and then at room temperature for further 3 hours. The resulting product was separated and purified according to the procedures as described in Example 1 to obtain 398 mg (Yield: 92%) of the title compound having the following structure as a red precipitate.

$^1$H-NMR (CDCl$_3$, δ ppm): 12.68(s, 1H), 12.49(s, 1H), 7.29(s, 2H), 7.26(d, J=1.0 Hz, 1H), 6.28(m, 1H), 5.26(m, 1H), 2.81(m, 2H), 1.80(s, 3H), 1.71(s, 3H)

$^{13}$C-NMR (CDCl$_3$, δ ppm): 174.9, 173.2, 170.4, 169.9, 160.7, 145.1, 137.3, 134.0, 133.7, 130.8, 116.5, 111.8, 111.6, 89.5, 74.4, 32.9, 25.8, 18.0

IR: 2920, 1765, 1610, 1230

MASS (rel. int.): 433(M$^+$, 0.5), 366(4), 364(5), 270(89), 255(42), 228(8), 219(5), 191(4), 120(25), 86(66), 84(100), 69(92)

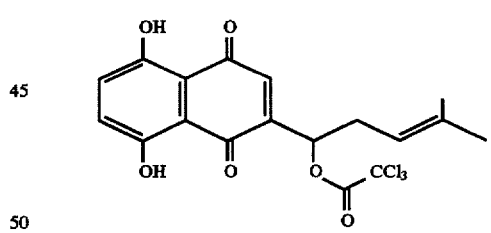

EXAMPLE 4

Preparation of 2-(1-n-propionyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 74 mg (1 mmole) of n-propionic acid at 0° C. under nitrogen gas, and the mixture was stirred for 30 minutes and then at room temperature for further 3 hours. The resulting product was separated and purified according to the procedures as described in Example 1 to obtain 210 mg (Yield: 61%) of the title compound having the following structure as a red precipitate.

¹H-NMR (CDCl₃, δ ppm): 12.58(s, 1H), 12.42(s, 1H), 7.18(s, 2H), 6.98(d, J=1.0 Hz, 1H), 6.02(m, 1H), 5.12(m, 1H), 2.52(m, 2H), 2.42(q, J=7.7 Hz, 2H), 1.69(s, 3H), 1.58(s, 3H), 1.18(t, J=7.7 Hz, 3H)

¹³C-NMR (CDCl₃, δ ppm): 178.3, 176.8, 173.1, 167.3, 166.8, 148.4, 136.0, 132.8, 132.6, 131.4, 117.7, 111.8, 111.5, 69.2, 32.8, 27.6, 25.7, 17.9, 9.0

IR: 2910, 1740, 1610, 1450

MASS (rel. int.): 344(M⁺, 0.5) 310(9) 271(29) 270(72) 220(49), 219(40), 189(13), 149(10), 137(11), 91(32), 77(18), 57(100)

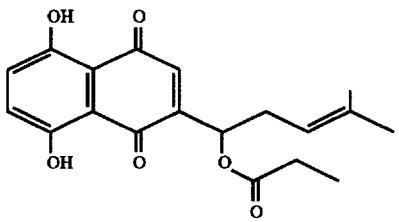

EXAMPLE 5

Preparation of 2-(1-n-butanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 88 mg (1 mmole) of n-butanoic acid at 0° C. under nitrogen gas, and the mixture was stirred for 30 minutes and then at room temperature for further 3 hours. The resulting product was separated and purified according to the procedures as described in Example 1 to obtain 186 mg (Yield: 52%) of the title compound having the following structure as a red oil.

¹H-NMR (CDCl₃, δ ppm): 12.59(s, 1H), 12.43(s, 1H), 7.19(s, 2H), 6.99(s, J=0.9 Hz, 1H), 6.04(m, 1H), 5.13(m, 1H), 2.52(m, 2H), 2.38(t, J=7.5 Hz, 2H), 1.69(s, 3H), 1.58(s, 3H), 1.26(m, 2H), 0.97(t, J=7.5 Hz, 3H)

¹³C-NMR (CDCl₃, δ ppm): 178.3, 176.8, 172.3, 167.3, 166.7, 148.4, 135.9, 132.8, 132.6, 131.4, 117.8, 111.8, 111.5, 69.2, 36.1, 32.9, 25.7, 18.4, 17.9, 13.6

IR: 2950, 1740, 1610, 1450

MASS (rel. int.): 358(M⁺, 1), 340(3) 270(29) 255(16) 220(13) 190(4), 137(6), 108(6), 91(6), 71(100), 43(100)

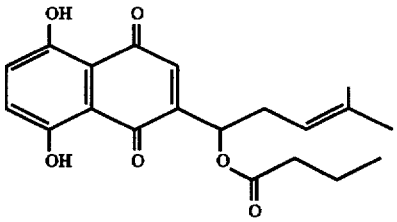

EXAMPLE 6

Preparation of 2-(1-isobutanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 88 mg (1 mmole) of isobutanoic acid at 0° C. under nitrogen gas, and the mixture was stirred for 30 minutes and then at room temperature for further 3 hours. The resulting product was separated and purified according to the procedures as described in Example 1 to obtain 161 mg (Yield: 45%) of the title compound having the following structure as a red oil.

¹H-NMR (CDCl₃, δ ppm): 12.58(s, 1H), 12.42(s, 1H), 7.18(s, 2H), 6.97(d, J=1.0 Hz, 1H), 6.01(m, 1H), 5.12(m, 1H), 2.75–2.45(m, 3H), 1.69(s, 3H), 1.58(s, 3H), 1.21(d, J=7.7 Hz, 6H)

¹³C-NMR (CDCl₃, δ ppm): 178.3, 176.8, 175.8, 167.3, 166.8, 148.5, 136.0, 132.8, 132.6, 131.3, 117.8, 111.8, 111.6, 69.0, 34.0, 33.0, 25.7, 18.9, 18.8, 18.0

IR: 2950, 1740, 1610, 1450

MASS (rel. int.): 358(M⁺, 2), 288(2), 271(50), 270(58), 255(26), 220(21), 189(6), 137(5), 89(5), 71(100)

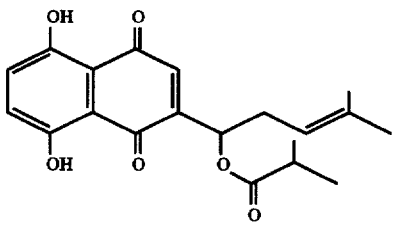

EXAMPLE 7

Preparation of 2-(1-n-hexanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 116 mg (1 mmole) of n-hexanoic acid at 0° C. under nitrogen gas, and the mixture was stirred for 30 minutes and then at room temperature for further 3 hours. The resulting product was separated and purified according to the procedures as described in Example 1 to obtain 150 mg (Yield: 39%) of the title compound having the following structure as a red precipitate.

¹H-NMR (CDCl₃, δ ppm): 12.50(s, 1H), 12.34(s, 1H), 7.09(s, 2H), 6.91(d, J=0.8 Hz, 1H), 5.96(m, 1H), 5.05(m, 1H), 2.44(m, 2H), 2.32(t, J=7.2 Hz, 2H), 1.62(s, 3H), 1.51(s, 3H), 1.35–0.76(m, 9H)

¹³C-NMR (CDCl₃, δ ppm): 178.3, 176.7, 172.5, 167.3, 166.8, 148.4, 135.9, 132.8, 132.6, 131.4, 117.8, 111.8, 111.5, 69.2, 34.2, 32.9, 31.2, 25.7, 24.6, 22.3, 17.9, 13.8

IR: 2950, 1740, 1610, 1450

MASS (rel. int.): 386(M⁺, 0.5), 288(2), 271(16), 270(55), 255(16), 220(14), 190(2), 99(100), 71(31), 60(16)

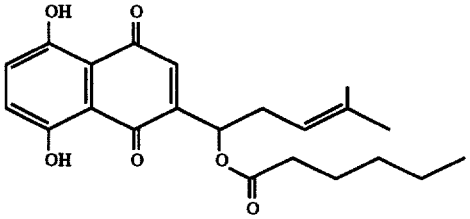

EXAMPLE 8

Preparation of 2-[1-(4-pentenoyl)oxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 100 mg (1 mmole) of 4-pentenoic acid at 0° C. under nitrogen gas, and the mixture was stirred for 30 minutes and then at room temperature for further 3 hours. The resulting product was separated and purified according to the procedures as described in Example 1 to obtain 155 mg (Yield: 42%) of the title compound having the following structure as a red precipitate.

$^1$H-NMR (CDCl$_3$, δ ppm) 12.48(s, 1H), 12.32(s, 1H), 7.08(s, 2H), 6.90(d, J=1.1 Hz, 1H), 6.05–5.60(m, 2H), 5.15–4.85(m, 3H), 2.60–2.30(m, 6H), 1.61(s, 3H), 1.50(s, 3H)

$^{13}$C-NMR (CDCl$_3$, δ ppm): 178.1, 176.6, 171.7, 167.4, 166.9, 148.2, 136.3, 136.0, 132.8, 132.6, 131.5, 117.8, 115.8, 111.8, 111.5, 69.4, 33.4, 32.9, 28.7, 25.7, 17.9

IR: 2910, 1740, 1610, 1450

MASS (rel. int.): 370(M$^+$, 3), 271(100) 270(100), 255 (58), 220(49), 190(10), 163(5), 137(8), 108(9), 83(100), 55(100)

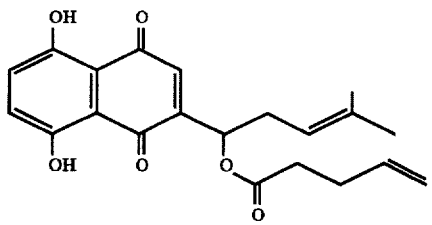

EXAMPLE 9

Preparation of 2-[1-(3,3-dimethyl)acryloxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 100 mg (1 mmole) of 3,3-dimethylacrylic acid at 0° C. under nitrogen gas, and the mixture was stirred for 30 minutes and then at room temperature for further 3 hours. The resulting product was separated and purified according to the procedures as described in Example 1 to obtain 229 mg (Yield: of the title compound having the following structure as a red precipitate.

$^1$H-NMR (CDCl$_3$, δ ppm): 12.59(s, 1H), 12.42(s, 1H), 7.27(s, 2H), 6.97(d, J=1.1 Hz, 1H), 6.00(m, 1H), 5.79(s, 1H), 5.14(m, 1H), 2.51(m, 1H), 2.15(s, 3H), 1.93(s, 3H), 1.68(s, 3H), 1.56(s, 3H)

$^{13}$C-NMR (CDCl$_3$, δ ppm): 179.0, 177.5, 166.8, 165.3, 158.9, 149.0, 135.8, 132.6, 132.4, 131.6, 118.0, 115.3, 111.9, 111.6, 68.6, 60.4, 32.9, 27.7, 25.7, 20.3, 18.0

IR: 2900, 1720, 1605, 1450

MASS (rel. int.): 392(M$^+$, 1) 353(4) 270(34) 254(3), 83(100)

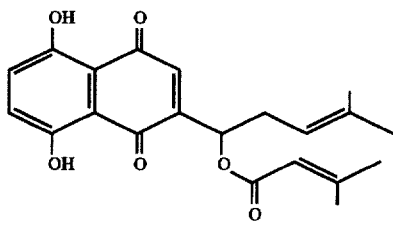

EXAMPLE 10

Preparation of 2-(1-phenylacetyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 136 mg (1 mmole) of phenylacetic acid at 0° C. under nitrogen gas, and the mixture was stirred for 30 minutes and then at room temperature for further 3 hours. The resulting product was separated and purified according to the procedures as described in Example 1 to obtain 239 mg (Yield: 59%) of the title compound having the following structure as a red precipitate.

$^1$H-NMR (CDCl$_3$, δ ppm): 12.55(s, 1H), 12.39(s, 3H), 7.45–7.30(m, 5H), 7.17(s, 2H), 6.78(d, J=0.9 Hz, 1H), 6.02(m, 1H), 5.03(m, 1H), 3.69(s, 2H), 2.48(m, 2H), 1.64(s, H), 1.53 (s, 3H)

$^{13}$C-NMR (CDCl$_3$, δ ppm): 177.9, 176.5, 170.2, 167.5, 166.9, 147.9, 136.0, 133.5, 132.9, 132.6, 131.3, 129.2, 128.7, 127.3, 117.6, 111.8, 111.5, 69.8, 41.5, 32.8, 25.7, 17.8

IR: 2925, 1740, 1605, 1450

MASS (rel. int.): 406(M$^+$, 3), 388(8), 271(22), 270(98), 255(20), 220(20), 219(16), 136(16), 118(25), 91(100), 84(25), 69(16)

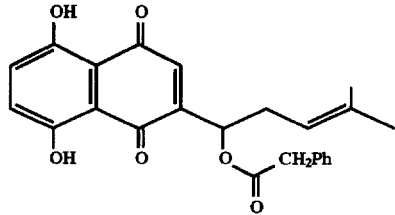

EXAMPLE 11

Preparation of 2-[1-trans-(2-hexenoyl)oxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 114 mg (1 mmole) of trans-2-hexenoic acid at 0° C. under nitrogen gas, and the mixture was stirred for 30 minutes and then at room temperature for further 3 hours. The resulting product was separated and purified according to the procedures as described in Example 1 to obtain 150 mg (Yield: 38%) of the title compound having the following structure as a red precipitate.

$^1$H-NMR (CDCl$_3$, δ ppm): 12.59(s, 1H), 12.43(s, 1H), 7.28–6.90(m, 1H), 7.18(s, 2H), 6.99(d, J=1.0 Hz, 1H), 6.20–5.80(m, 2H), 5.14(m, 1H), 3.47(q, J=7.2 Hz, 2H), 2.80–1.70(m, 15H)

$^{13}$C-NMR (CDCl$_3$, δ ppm): 178.7, 177.2, 167.0, 166.5, 165.3, 150.9, 148.6, 135.0, 132.7, 132.5, 131.6, 120.6, 117.8, 111.8, 111.5, 69.2, 34.3, 32.9, 39.7, 29.2, 17.9, 13.7

IR: 2900, 1720, 1610, 1450

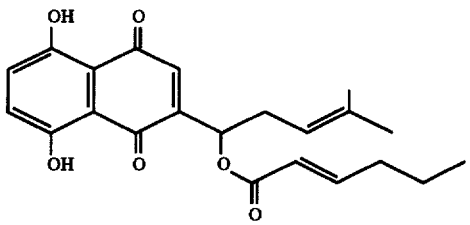

EXAMPLE 12

Preparation of 2-[1-trans-(3-hexenoyl)oxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 114 mg (1 mmole) of trans-3-hexenoic acid at 0° C. under nitrogen gas, and the mixture was stirred for 30 minutes and then at room temperature for further 3 hours. The resulting product was separated and purified according to the procedures as described in Example 1 to obtain 115 mg (Yield: 30%) of the title compound having the following structure as a red precipitate.

$^1$H-NMR (CDCl$_3$, δ ppm): 12.56(s, 1H), 12.41(s, 1H), 7.16(s, 2H), 6.98(d, J=0.9 Hz, 1H), 6.02(m, 1H), 5.85–5.30 (m, 2H), 5.13(s, 1H), 3.10(d, J=5.5 Hz, 2H), 2.56(m, 2H), 2.07(m, 2H), 1.69(s, 3H), 1.59(s, 3H), 1.01(t, J=7.2 Hz, 3H)

$^{13}$C-NMR (CDCl$_3$, δ ppm): 178.2, 176.7, 170.8, 167.4, 166.8, 148.2, 136.9, 136.0, 132.8, 132.6, 131.4, 119.9, 117.7, 111.8, 111.5, 69.5, 38.0, 32.8, 25.7, 25.5, 17.9, 13.4

IR: 2950, 1740, 1605, 1450

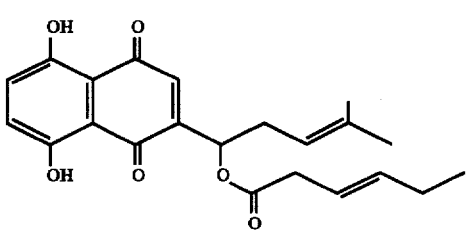

EXAMPLE 13

Preparation of 2-[1-(6-heptenoyl)oxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 128 mg (1 mmole) of 6-heptenoic acid at 0° C. under nitrogen gas, and the mixture was stirred for 30 minutes and then at room temperature for further 3 hours. The resulting product was separated and purified according to the procedures as described in Example 1 to obtain 175 mg (Yield: 44%) of the title compound having the following structure as a red precipitate.

$^1$H-NMR (CDCl$_3$, δ ppm): 12.55(s, 1H), 12.39(s, 1H), 7.15(s, 2H), 6.97(d, J=1.0 Hz, 1H), 6.15–5.65(m, 2H), 5.13–4.89(m, 3H), 2.80–2.00(m, 6H), 1.69(s, 3H), 1.58(s, 3H), 2.80–1.50 (m, 2H)

$^{13}$C-NMR (CDCl$_3$, δ ppm): 178.1, 176.6, 172.2, 167.3, 166.7, 148.3, 138.1, 135.8, 132.7, 132.5, 131.3, 117.8, 114.7, 111.7, 111.4, 34.0, 33.2, 32.8, 28.2, 25.6, 24.3, 17.8

IR: 2925, 1740, 1605, 1450

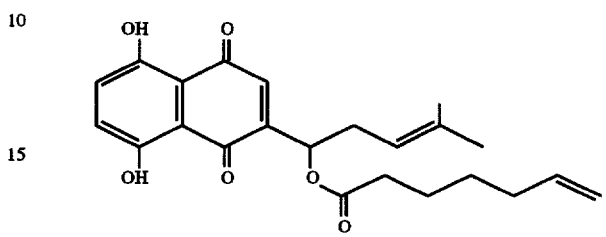

EXAMPLE 14

Preparation of 2-(1-n-octanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 144 mg (1 mmole) of n-octanoic acid at 0° C. under nitrogen gas, and the mixture was stirred for 30 minutes and then at room temperature for further 3 hours. The resulting product was separated and purified according to the procedures as described in Example 1 to obtain 174 mg (Yield: 42%) of the title compound having the following structure as a red oil.

$^1$H-NMR (CDCl$_3$, δ ppm): 12.55(s, 1H), 12.38(s, 1H), 7.15(s, 2H), 6.97(d, J=1.0 Hz, 1H), 6.03(m, 1H), 5.13(m, 1H), 2.51(m, 2H), 2.40(t, J=7.5 Hz, 2H), 1.69(s, 3H), 1.58(s, 3H), 1.50–1.10(m, 10H), 0.88(t, J=6.0 Hz, 3H)

$^{13}$C-NMR (CDCl$_3$, δ ppm): 178.3, 176.8, 172.4, 167.1, 166.6, 148.4, 135.8, 132.6, 132.5, 131.4, 117.8, 111.7, 111.5, 69.1, 34.2, 32.8, 31.6, 29.0, 28.8, 25.6, 24.8, 22.5, 17.8, 13.9

IR: 2925, 1740, 1610, 1450

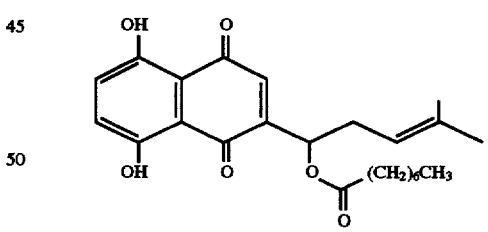

EXAMPLE 15

Preparation of 2-(1-n-nonanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 158 mg (1 mmole) of n-nonanoic acid at 0° C. under nitrogen gas, and the mixture was stirred for 30 minutes and then at room temperature for further 3 hours. The resulting product was separated and purified according to the procedures as described in Example 1 to obtain 231 mg (Yield: 54%) of the title compound having the following structure as a red oil.

¹H-NMR (CDCl₃, δ ppm) 12.54(s, 1H), 12.38(s, 1H), 7.15(s, 2H), 6.97(d, J=1.0 Hz, 1H), 6.03(m, 1H), 5.13(m, 1H), 2.51(m, 2H), 2.39(t, J=7.2 Hz, 2H), 1.68(s, 3H), 1.58(s, 3H), 1.50–1.10(m, 12H), 0.87(t, J=6.3 Hz, 3H)

¹³C-NMR (CDCl₃, δ ppm): 178.2, 176.8, 172.4, 167.2, 166.6, 148.4, 135.8, 132.6, 132.5, 131.4, 117.8, 111.7, 111.4, 69.1, 34.2, 32.8, 31.7, 31.4, 29.0, 25.6, 24.8, 2.5, 17.8, 13.9

IR: 2925, 1740, 1610, 1450

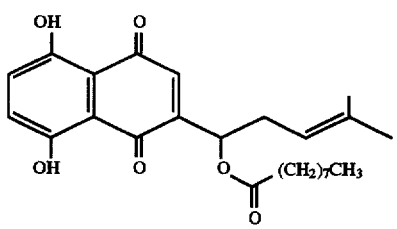

EXAMPLE 16

Preparation of 2-(1-n-decanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 172 mg (1 mmole) of n-decanoic acid at 0° C. under nitrogen gas, and the mixture was stirred for 30 minutes and then at room temperature for further 3 hours. The resulting product was separated and purified according to the procedures as described in Example 1 to obtain 217 mg (Yield: 49%) of the title compound having the following structure as a red oil.

¹H-NMR (CDCl₃, δ ppm): 12.55(s, 1H), 12.39(s, 1H), 7.15(s, 2H), 6.98(d, J=0.9 Hz, 1H), 6.03(m, 1H), 5.13(m, 1H), 2.52(m, 2H), 2.40(t, J=7.3 Hz, 2H), 1.69(s, 3H), 1.59(s, 3H), 1.50–1.10(m, 14H), 0.88(t, J=6.0 Hz, 3H)

¹³C-NMR (CDCl₃, δ ppm): 178.3, 176.8, 172.4, 167.2, 166.7, 148.4, 135.8, 132.7, 132.5, 131.4, 117.8, 111.8, 111.5, 69.1, 34.2, 32.9, 31.8, 29.3, 29.2, 29.1, 29.0, 25.6, 24.9, 22.6, 17.8, 14.0

IR: 2925, 1740, 1610, 1450

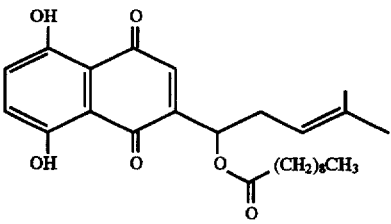

EXAMPLE 17

Preparation of 2-(1-lauryloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 200 mg (1 mmole) of lauric acid at 0° C. under nitrogen gas, and the mixture was stirred for 30 minutes and then at room temperature for further 3 hours. The resulting product was separated and purified according to the procedures as described in Example 1 to obtain 202 mg (Yield: 43%) of the title compound having the following structure as a red precipitate.

¹H-NMR (CDCl₃, δ ppm): 12.57(s, 1H), 12.41(s, 1H), 7.17(m, 1H), 6.98(d, J=0.9 Hz, 1H), 6.02(m, 1H), 5.12(m, 1H), 2.51(m, 2H), 2.39(t, J=7.5 Hz, 2H), 1.68(s, 3H), 1.58(s, 3H), 1.55–1.10(m, 18H), 0.88(t, J=6.0 Hz, 3H)

¹³C-NMR (CDCl₃, δ ppm): 178.2, 176.7, 172.4, 167.4, 166.8, 148.4, 135.9, 132.8, 132.6, 131.4, 117.8, 111.8, 111.5, 69.2, 34.3, 32.9, 31.8, 31.5, 29.5(2C), 29.4, 29.2, 29.1, 25.7, 24.9, 22.6, 17.9, 14.0

IR: 1740, 1610, 1450

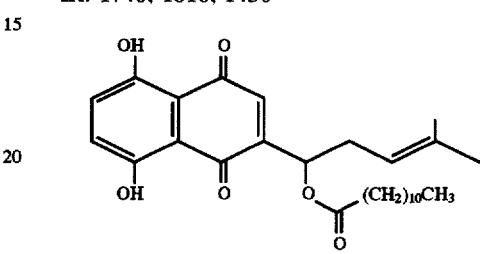

EXAMPLE 18

Preparation of 2-(1-diphenylacetyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 212 mg (1 mmole) of diphenylacetic acid at 0° C. under nitrogen gas, and the mixture was stirred for 30 minutes and then at room temperature for further 3 hours. The resulting product was separated and purified according to the procedures as described in Example 1 to obtain 270 mg (Yield: 59%) of the title compound having the following structure as a red precipitate.

¹H-NMR (CDCl₃, δ ppm): 12.56(s, 1H), 12.38(s, 1H), 7.33(s, 10H), 7.17(s, 2H), 6.66(d, J=0.8 Hz, 1H), 6.09(m, 1H), 5.11(s, 1H), 5.04(m, 1H), 2.48(m, 2H), 1.63(s, 3H), 1.52(s, 3H)

¹³C-NMR (CDCl₃, δ ppm): 177.7, 176.2, 171.1, 167.6, 167.1, 147.7, 138.1, 137.8, 136.0, 132.9, 131.2, 129.5, 129.4, 129.1, 129.0, 128.7, 128.6, 128.2, 127.7, 127.5, 127.4, 117.7, 111.7, 111.5, 70.0, 57.1, 32.9, 25.6, 17.8

IR: 2925, 1740, 1605, 1450

MASS (rel. int.): 482(M⁺, 0.5), 293(6), 270(14), 168(28), 167(100), 166(40), 152(25), 149(44), 127(11), 105(10), 86(29), 84(53), 71(28), 55(46)

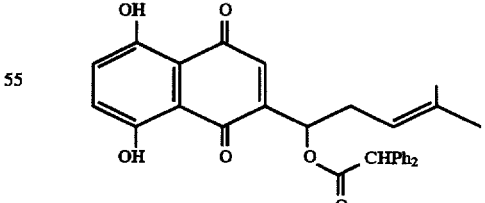

EXAMPLE 19

Preparation of 2-(1-undecylenoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 184 mg (1 mmole) of undecylenic acid at 0° C. under nitrogen gas, and the mixture was stirred for 30 minutes and then at room temperature for further 3 hours. The resulting product was separated and purified according to the procedures as described in Example 1 to obtain 172 mg (Yield: 38%) of the title compound having the following structure as a red oil.

$^1$H-NMR (CDCl$_3$, δ ppm): 12.57(s, 1H), 12.41(s, 1H), 7.16(s, 2H), 6.95(d, J=1.1 Hz, 1H), 6.00(m, 1H), 5.70(m, 1H), 5.25–4.80(m, 3H), 2.50(m, 2H), 2.40–0.83(m, 22H)

$^{13}$C-NMR (CDCl$_3$, δ ppm): 178.3, 176.8, 172.5, 167.4, 166.9, 148.4, 139.1, 135.9, 132.8, 132.6, 131.4, 117.8, 114.1, 111.8, 111.5, 69.2, 111.5, 69.2, 34.3, 33.7, 32.9, 29.7, 29.3, 29.2, 29.0, 28.8, 25.7, 24.9, 17.9

IR: 2925, 1740, 1605, 1450

MASS (rel. int.): 454(M$^+$, 1), 288(3), 271(34), 270(100), 255(24), 220(25), 167(6), 107(6), 81(13), 67(27)

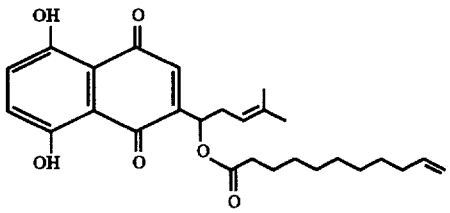

EXAMPLE 20

Preparation of 2-(1-stearyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 284 mg mmole) of stearic acid at 0° C. under nitrogen gas, and the mixture was stirred for 30 minutes and then at room temperature for further 3 hours. The resulting product was separated and purified according to the procedures as described in Example 1 to obtain 305 mg (Yield: 55%) of the title compound having the following structure as a red precipitate.

$^1$H-NMR (CDCl$_3$, δ ppm): 12.58(s, 1H), 12.42(s, 1H), 7.17(s, 2H), 6.98(d, J=1.0 Hz, 1H), 6.04(m, 1H), 5.12(m, 1H), 2.52(m, 2H), 2.39(t, J=7.6 Hz, 2H), 1.50–0.80(m, 33H)

$^{13}$C-NMR (CDCl$_3$, δ ppm): 178.43, 176.98, 172.5, 167.3, 166.7, 148.5, 135.9, 132.8, 132.6, 131.5, 117.8, 111.8, 111.5, 69.2, 34.3, 32.9, 32.7, 29.7, 29.5, 29.4, 29.3, 29.1, 25.7, 25.2, 24.9, 22.7, 17.9, 14.1

IR: 2925, 1740, 1610, 1450

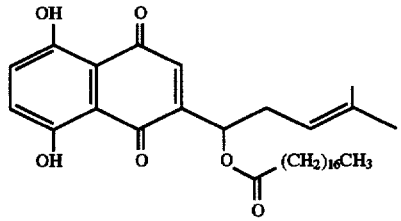

EXAMPLE 21

Preparation of 2-(1-palmityloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 256 mg (1 mmole) of palmitic acid at 0° C. under nitrogen gas, and the mixture was stirred for 30 minutes and then at room temperature for further 3 hours. The resulting product was separated and purified according to the procedures as described in Example 1 to obtain 305 mg (Yield: 58%) of the title compound having the following structure as a red precipitate.

$^1$H-NMR (CDCl$_3$, δ ppm): 12.65(s, 1H), 12.49(s, 1H), 7.05(s, 2H), 6.98(d, J=1.1 Hz, 1H), 6.03(m, 1H), 5.12(m, 1H), 2.52(m, 2H), 2.39(t, J=7.7 Hz, 2H), 1.69(s, 3H), 1.58(s, 3H), 1.43–0.80(m, 29H)

$^{13}$C-NMR (CDCl$_3$, δ ppm): 178.3, 176.8, 172.5, 167.3, 166.8, 148.5, 136.0, 132.8, 132.6, 131.5, 117.8, 111.8, 111.5, 69.2, 34.3, 32.9, 31.9, 31.8, 29.7, 29.5, 29.4, 29.3, 29.1, 29.0, 26.0, 25.7, 25.5, 25.0, 24.9, 23.0, 17.9, 14.1

IR: 2920, 1740, 1605, 1450

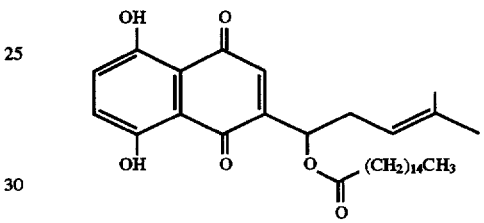

EXAMPLE 22

Preparation of 2-(1-oleyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 282 mg (1 mmole) of oleic acid at 0° C. under nitrogen gas, and the mixture was stirred for 30 minutes and then at room temperature for further 3 hours. The resulting product was separated and purified according to the procedures as described in Example 1 to obtain 265 mg (Yield: 48%) of the title compound having the following structure as a red oil.

$^1$H-NMR (CDCl$_3$, δ ppm): 12.58(s, 1H), 12.42(s, 1H), 7.18(s, 2H), 7.08(d, J=1.1 Hz, 1H), 6.03(m, 1H), 5.34(m, 2H), 5.12(m, 1H), 2.51(m, 2H), 2.39(t, J=7.5 Hz, 2H), 2.00(m, 4H), 1.69(s, 3H), 1.57(s, 3H), 1.56–0.85(m, 25H)

$^{13}$C-NMR (CDCl$_3$, δ ppm): 178.3, 176.8, 172.3, 167.1, 166.5, 148.4, 135.8, 132.6, 132.4, 131.4, 130.0, 129.6, 117.8, 117.1, 111.4, 69.1, 34.2, 32.8, 31.8, 29.7, 29.6, 29.4, 29.2, 29.1, 29.0, 27.1, 25.6, 24.8, 22.6, 17.8, 14.0

IR: 2925, 1740, 1605, 1450

MASS (rel. int.): 552(M$^+$, 2), 288(3), 271(28), 270(100), 255(22), 229(13), 220(18), 151(6), 111(20), 97(37), 83(37)

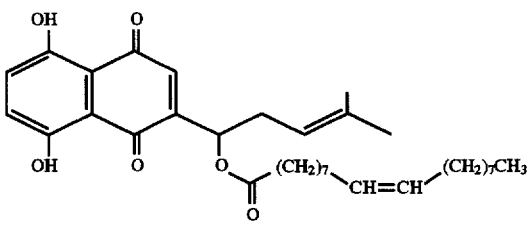

EXAMPLE 23

Preparation of 2-(1-linolenyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 278 mg (1 mmole) of linolenic acid at 0° C. under nitrogen gas, and the mixture was stirred for 30 minutes and then at room temperature for further 3 hours. The resulting product was separated and purified according to the procedures as described in Example 1 to obtain 230 mg (Yield: 42%) of the title compound having the following structure as a red precipitate.

$^1$H-NMR (CDCl$_3$, δ ppm): 12.58(s, 1H), 12.43(s, 1H), 7.18(s, 2H), 6.98(d, J=1.0 Hz, 1H), 6.03(m, 1H), 5.43–5.12 (m, 7H), 2.86–0.80(m, 31H)

$^{13}$C-NMR (CDCl$_3$, δ ppm): 178.2, 176.7, 172.4, 167.3, 166.7, 148.4, 135.9, 132.8, 132.6, 131.8, 131.4, 130.2, 128.2, 127.7, 127.0, 117.8, 111.8, 111.5, 69.1, 34.2, 32.9, 29.5, 29.1, 29.0, 27.1, 25.7, 25.5, 25.4, 25.1, 24.9, 24.6, 20.5, 17.9, 14.2

IR: 2925, 1740, 1605, 1450

MASS (rel. int.): 548(M$^+$, 3), 288(3), 277(32), 272(69), 270(100), 255(39), 254(24), 220(25), 191(4), 149(11), 135 (20), 121(24), 108(53), 95(44), 79(60)

$^1$H-NMR (CDCl$_3$, δ ppm): 12.61(s, 1H), 12.43(s, 1H), 7.72(m, 1H), 7.17(s, 2H), 7.00(d, J=0.9 Hz, 1H), 6.45–5.80 (m, 5H), 5.17(m, 1H), 4.30(m, 1H), 2.60–0.80(m, 30H)

$^{13}$C-NMR (CDCl$_3$, δ ppm): 178.8, 177.3, 166.6, 166.1, 165.6, 154.5, 148.8, 140.0, 137.5, 137.0, 135.6, 134.6, 132.4, 132.2, 131.6, 131.5, 130.7, 129.9, 129.7, 129.2, 128.8, 128.6, 117.9, 117.1, 111.7, 111.4, 68.6, 60.2, 39.4, 32.9, 32.8, 29.1, 28.8, 25.6, 24.6, 21.6, 21.3, 20.8, 19.3, 19.1, 17.8, 14.0, 13.8, 12.8

IR: 2925, 1710, 1605, 1450

MASS (rel. int.): 570(M$^+$, 100) 444(12), 300(18), 299 (20), 272(11), 255(12), 29(16), 205(22), 201(19), 189(24), 176(23), 161(30), 149(16), 133(21), 119(33), 99(47), 81(20)

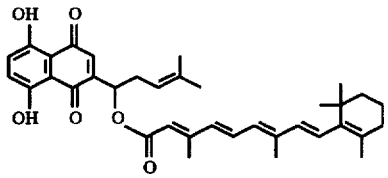

EXAMPLE 25

Preparation of 2-[1-(cis-retinoyl)oxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 300 mg (1 mmole) of cis-retinoic acid at 0° C. under nitrogen gas, and the mixture was stirred for 30 minutes and then at room temperature for further 3 hours. The resulting product was separated and purified according to the procedures as described in Example 1 to obtain 217 mg (Yield: 38%) of the title compound having the following structure as a red precipitate.

$^1$H-NMR (CDCl$_3$, δ ppm): 12.60(s, 1H), 12.42(s, 1H), 7.72(m, 1H), 7.16(s, 2H), 6.98(d, J=0.8 Hz, 1H), 6.40–5.70 (m, 5H), 5.17(m, 1H), 2.53(m, 2H), 2.40–0.80(m, 28H)

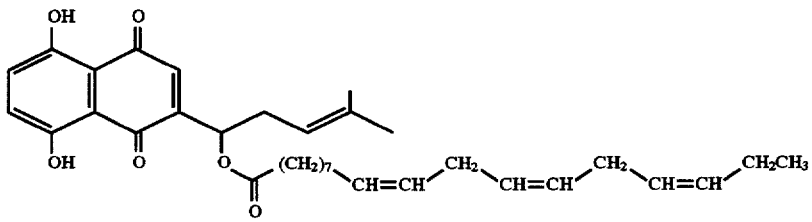

EXAMPLE 24

Preparation of 2-[1-trans-retinoyloxy)-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 300 mg (1 mmole) of trans-retinoic acid at 0° C. under nitrogen gas, and the mixture was stirred for 30 minutes and then at room temperature for further 3 hours. The resulting product was separated and purified according to the procedures as described in Example 1 to obtain 200 mg (Yield: 35%) of the title compound having the following structure as a red precipitate.

$^{13}$C-NMR (CDCl$_3$, δ ppm): 178.8, 177.4, 166.8, 166.2, 164.9, 153.0, 148.9, 140.3, 137.6, 137.3, 135.7, 133.2, 132.9, 132.5, 132.3, 131.6, 130.1, 129.3, 129.0, 128.8, 118.0, 115.2, 111.8, 111.5, 68.7, 39.6, 34.2, 33.1, 32.8, 28.9, 25.7, 21.7, 21.0, 19.2, 17.9, 12.8

IR: 2925, 1710, 1605, 1450

EXAMPLE 26

Preparation of 2-(1-n-pentanoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 102 mg (1 mmole) of n-pentanoic acid at 0° C. under nitrogen gas, and the mixture was stirred for 30 minutes and then at room temperature for further 3 hours. The resulting product was separated and purified according to the procedures as described in Example 1 to obtain 223 mg (Yield: 60%) of the title compound having the following structure as a red oil.

$^1$H-NMR (CDCl$_3$, δ ppm): 12.53(s, 1H), 12.37(s, 1H), 7.14(s, 2H), 6.97(d, J=1.0 Hz, 1H), 6.02(m, 1H), 5.13(m, 1H), 2.70–2.30(m, 4H), 1.68(s, 3H), 1.58(s, 3H), 1.50–1.10 (m, 4H), 0.93(t, J=6.2 Hz, 3H)

$^{13}$C-NMR (CDCl$_3$, δ ppm): 178.3, 176.8, 172.3, 167.0, 166.4, 148.3, 135.7, 132.6, 132.4, 131.3, 117.8, 111.6, 111.4, 69.0, 33.9, 32.8, 26.8, 25.6, 22.1, 17.7, 13.5

IR: 2950, 1740, 1610, 1450

MASS (rel. int.): 372(M$^+$, 1), 271(27), 270(59), 220(21), 85(100), 57(59)

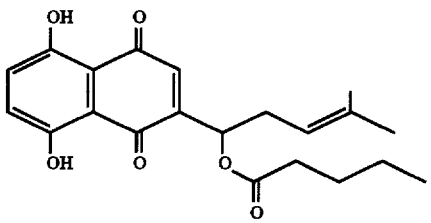

EXAMPLE 27

Preparation of 2-[1-(trans-2-pentenoyloxy)-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 100 mg (1 mmole) of n-pentenoic acid at 0° C. under nitrogen gas, and the mixture was stirred for 30 minutes and then at room temperature for further 3 hours. The resulting product was separated and purified according to the procedures as described in Example 1 to obtain 95 mg (Yield: 23%) of the title compound having the following structure as a red precipitate.

$^1$H-NMR (CDCl$_3$, δ ppm): 12.58(s, 1H), 12.42(s, 1H), 7.18(s, 2H), 7.12(m, 1H), 7.00(d, J=1.0 Hz, 1H), 6.08(m, 1H), 5.88(m, 1H), 5.14(m, 1H), 2.55(m, 2H), 2.28(m, 2), 1.69(s, 3H), 1.11(t, J=7.2 Hz, 3H)

$^{13}$C-NMR (CDCl$_3$, δ ppm): 178.7, 177.2, 167.0, 166.5, 165.3, 152.2, 148.5, 135.9, 132.6, 132.5, 131.5, 119.6, 117.8, 111.8, 111.5, 69.2, 32.8, 25.7, 25.4, 17.9, 12.0

IR: 2925, 1720, 1610, 1450

MASS (rel. int.): 370(M$^+$, 2), 288(6), 271(49), 270(100), 255(65), 220(14), 137(4), 97(13), 83(100)

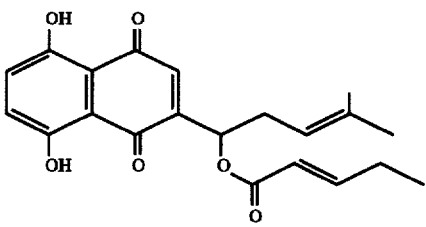

EXAMPLE 28

Preparation of 2-[1-(2,4-hexadienoyloxy)-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of dimethylaminopyridine were dissolved in 3 ml of dry dichloromethane. To the resulting solution was added 112 mg (1 mmole) of 2,4-hexadienoic acid at 0° C. under nitrogen gas, and the mixture was stirred for 30 minutes and then at room temperature for further 3 hours. The resulting product was separated and purified according to the procedures as described in Example 1 to obtain 152 mg (Yield: 40%) of the title compound having the following structure as a red precipitate.

$^1$H-NMR (CDCl$_3$, δ ppm): 12.57(s, 1H), 12.40(s, 1H), 7.30(m, 1H), 7.16(s, 2H), 6.99(d, J=1.0 Hz, 1H), 6.35–5.75 (m, 4H), 5.15(m, 1H), 2.56(m, 2H), 1.86(d, J=5.1 Hz, 3H), 1.67(s, 3H), 1.58(s, 3H)

$^{13}$C-NMR (CDCl$_3$, δ ppm): 178.6, 177.2, 167.0, 166.4, 165.8, 148.5, 146.1, 140.3, 135.8, 132.6, 132.4, 131.5, 129.6, 118.1, 117.8, 111.8, 11.5, 69.2, 32.9, 25.7, 18.6, 17.9

IR: 2925, 1740, 1610, 1450

MASS (rel int.): 382(M$^+$, 11), 334(25), 271(20), 270(25), 254(26), 229(16), 112(78), 97(100), 67(60)

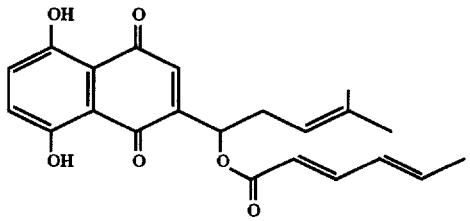

EXAMPLE 29

Preparation of 2-[1-(trans-2,6-heptadienoyloxy)-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 124 mg (1 mmole) of 2,6-trans-heptanoic acid at 0° C. under nitrogen gas, and the mixture was stirred for 30 minutes and then at room temperature for further 3 hours. The resulting product was separated and purified according to the procedures as described in Example 1 to obtain 125 mg (Yield: of the title compound having the following structure as a red precipitate.

$^1$H-NMR (CDCl$_3$, δ ppm): 12.57(s, 1H), 12.40(s, 1H), 7.15–7.00(m, 1H), 7.17(s, 2H), 6.97(d, J=1.0 Hz, 1H), 6.20–5.60(m, 3H), 5.30–4.80(m, 3H), 2.90–2.10(m, 6H), 1.68(s, 3H), 1.57(s, 3H)

$^{13}$C-NMR (CDCl$_3$, δ ppm): 178.5, 177.0, 167.1, 166.6, 165.1, 149.8, 148.5, 136.8, 135.9, 132.7, 132.5, 131.5, 121.0, 117.8, 115.7, 111.6, 111.5, 69.3, 32.9, 31.9, 25.7, 17.9

IR: 2925, 1720, 1605, 1450

MASS (rel int.): 396(M$^+$, 2), 288(4), 271(42), 270(100), 255(44), 220(6), 109(100), 81(45)

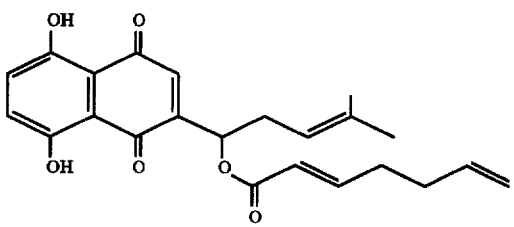

EXAMPLE 30

Preparation of 2-(1-benzoyloxy-4-methyl-3-pentenyl)-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 122 mg (1 mmole) of benzoic acid at 0° C. under nitrogen gas, and the mixture was stirred for 30 minutes and then at room temperature for further 3 hours. The resulting product was separated and purified according to the procedures as described in Example 1 to obtain 117 mg (Yield: 30%) of the title compound having the following structure as a red precipitate.

$^1$H-NMR (CDCl$_3$, δ ppm): 12.61(s, 1H), 12.40(s, 1H), 8.30–7.30(m, 5H), 7.18(s, 2H), 7.06(d, J=1.0 Hz, 1H), 6.27(m, 1H), 5.22(m, 1H), 2.68(m, 2H), 1.69(s, 3H), 1.61(s, 3H)

$^{13}$C-NMR (CDCl$_3$, δ ppm): 177.9, 176.5, 167.7, 167.2, 165.3, 148.2, 136.2, 133.4, 132.9, 132.8, 131.4, 130.4, 129.7, 128.5, 117.7, 111.8, 111.0, 70.0, 33.0, 25.7, 18.0

IR: 2925, 1740, 1605, 1450

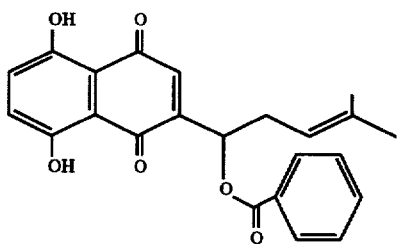

EXAMPLE 31

Preparation of 2-[1-(9,12-octadecadinoyloxy-4-methyl-3-pentenyl]-5,8-dihydroxy-1,4-naphthoquinone 288 mg (1 mmole) of shikonin, 226 mg (1.1 mmole) of dicyclohexylcarbodiimide and 30 mg (0.25 mmole) of 4-dimethylaminopyridine were dissolved in 3 ml of dry dichloromethane. To the resulting solution was added 280 mg (1 mmole) of 9,12-octadecadienoic acid at 0° C. under nitrogen gas, and the mixture was stirred for 30 minutes and then at room temperature for further 3 hours. The resulting product was separated and purified according to the procedures as described in Example 1 to obtain 210 mg (Yield: of the title compound having the following structure as a red oil.

$^1$H-NMR (CDCl$_3$, δ ppm): 12.56(s, 1H), 12.40(s, 1H), 7.17(s, 2H), 6.97(d, J=1.0 Hz, 1H), 6.02(m, 1H), 5.38(m, 4H), 5.12(m, 1H), 2.90–1.80(m, 10H), 1.67(s, 3H), 1.57(s, 3H), 1.50–0.70(m, 19H)

$^{13}$C-NMR (CDCl$_3$, δ ppm): 178.2, 176.7, 172.4, 167.3, 166.8, 148.4, 135.9, 132.7, 132.6, 131.4, 130.1, 129.9, 128.0, 127.8, 117.8, 111.8, 111.5, 69.1, 34.2, 32.9, 31.4, 29.5, 29.3, 29.0, 27.1, 25.7, 25.6, 24.8, 22.5, 17.9, 14.0

IR: 2920, 1740, 1605, 1450

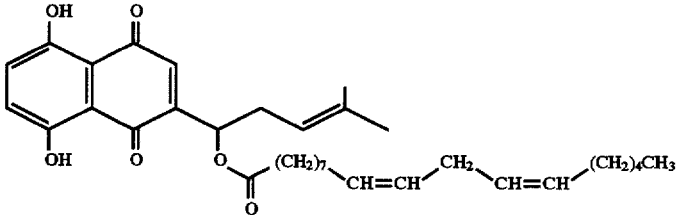

EXAMPLE 32

Preparation of 2-(1-hydroxypentyl)-5,8-dimethoxy-1,4-naphthoquinone 3.6 g (10.3 mmole) of 2-(1-hydroxyhexyl)-1,4,5,8-tetramethoxynaphthalene was dissolved in 50 ml of acetonitrile and then a solution of 14.2 g (25.0 mmole) of cerium (IV) ammonium nitrate dissolved in 50 ml of distilled water was added dropwise thereto over 30 minutes through a dropping funnel in a cooling bath (0°–5° C.). The reaction mixture was stirred at normal temperature for 2 hours. After adding 100 ml of distilled water thereto, the reaction mixture was extracted twice with dichloromethane solvent, dried over anhydrous magnesium sulfate and then filtered through filter paper. The resulting filtrate was concentrated under reduced pressure to obtain a crude product. The crude product was purified by silica gel column chromatography (silica gel 4.0×15 cm) using the solvent condition which increases the amount of ethylacetate so that the n-hexane/ethylacetate ratio can vary from 5:1 to 1:3, to obtain 1.2 g of the title compound as a yellow precipitate.

Yield: 48%

TLC (h-hexane:ethylacetate=1:2): Rf=0.34

Melting Point: 67.5°–69.0° C.

$^1$H-NMR (CDCl$_3$, δ ppm): 7.30(s, 2H), 6.77(s, 1H), 4.75(m, 1H), 3.95(s, 6H), 2.86(br.s, 1H), 1.67(m, 2H), 1.55–1.15(m, 4H), 0.89(t, J=6.0 Hz, 3H)

$^{13}$C-NMR (CDCl$_3$, δ ppm): 185.3, 184.9, 153.8, 153.4, 151.2, 133.4, 121.1, 120.8, 120.5, 120.1, 69.1, 56.8, 56.7, 36.1, 27.9, 22.4, 13.9

IR: 3470, 2950, 1645, 1470

MASS: 304(M$^+$, 62), 289(100), 275(65), 257(24), 247(90), 233(61), 219(34), 204(8), 191(10), 173(8), 121(4), 85(17)

EXAMPLE 33

Preparation of 2-(1-hydroxyhexyl)-5,8-dimethoxy-1,4-naphthoquinone

According to the same procedure as Example 32, 2-(1-hydroxyhexyl)-1,4,5,8-tetramethoxynaphthalene was used to obtain 2.1 g of the title compound as a yellow oil.

Yield: 64%

TLC (n-hexane:ethylacetate=1:2): Rf=0.19

$^1$H-NMR (CDCl$_3$, δ ppm): 7.30(s, 2H), 6.76(d, J=1.1 Hz, 1H), 4.72(m, 1H), 3.95(s, 6H), 2.90(d, J=5.4 Hz, 1H), 1.66(m, 2H), 1.55–1.10(m, 6H), 0.87(t, J=6.0 Hz, 3H)

$^{13}$C-NMR (CDCl$_3$, δ ppm): 185.2, 184.9, 153.7, 153.3, 151.2, 133.3, 121.0, 120.7, 120.4, 120.1, 68.9, 56.7, 56.6, 36.3, 31.4, 25.4, 22.4, 13.9 IR: 3475, 2925, 1645, 1470

MASS: 318(M$^+$, 24) 303(82) 289(40), 257(19), 247 (100), 233(33), 219(48), 204(29), 187(13), 173(10), 99(37), 84(6)

EXAMPLE 34

Preparation of 2-(1-hydroxyoctyl)-5,8-dimethoxy-1,4-naphthoquinone

According to the same procedure as Example 32, 2-(1-hydroxyoctyl)-1,4,5,8-tetramethoxynaphthalene was used to obtain 3.51 g of the title compound as a yellow precipitate.

Yield: 40%

TLC (n-hexane:ethylacetate=1:2): Rf=0.39

$^1$H-NMR (CDCl$_3$, δ ppm): 7.30(s, 2H), 6.77(d, J=1.0 Hz, 1H), 4.75(m, 1H), 3.94(s, 6H), 2.99(br.s, 1H), 1.61(m, 2H), 1.50–1.05(m, 10H), 0.86(t, J=6.0 Hz, 3H)

$^{13}$C-NMR (CDCl$_3$, δ ppm): 185.2, 184.9, 153.7, 153.3, 151.4, 133.3, 120.7, 120.4, 120.1, 119.7, 68.8, 56.7, 56.6, 36.5, 31.7, 29.2, 29.0, 25.7, 22.5, 13.9

IR: 3475, 2925, 1645, 1560, 1470

MASS: 346(M$^+$, 23), 331(100), 317(32), 247(51), 243 (15), 219(13), 205(5), 84(11), 57(2)

EXAMPLE 35

Preparation of 2-(1-hydroxydecyl)-5,8-dimethoxy-1,4-naphthoquinone

According to the same procedure as Example 32, 2-(1-hydroxydecyl)-1,4,5,8-tetramethoxynaphthalene was used to obtain 2.32 g of the title compound as a yellowish red oil.

Yield: 60%

TLC (n-hexane:ethylacetate=1:2): Rf=0.26

$^1$H-NMR (CDCl$_3$, δ ppm): 7.29(s, 2H), 6.76(d, J=0.9 Hz, 1H), 4.75(m, 1H), 3.94(s, 6H), 2.86(br.s, 1H), 1.70(m, 2H), 1.55–1.05(m, 14H), 0.86(t, J=6.0 Hz, 3H)

$^{13}$C-NMR (CDCl$_3$, δ ppm): 185.2, 184.9, 153.7, 153.3, 151.4, 133.3, 121.0, 120.7, 120.4, 120.1, 68.8, 56.6(2C), 36.5, 31.7, 29.4, 29.3(2C), 29.1, 25.7, 22.5, 14.0

IR: 3475, 2925, 1645, 1470

MASS: 374(M$^+$, 15), 360(76), 359(75), 345(32), 247 (100), 233(27), 219(29), 204(12), 191(7), 84(21)

EXAMPLE 36

Preparation of 2-(1-hydroxytridecyl)-5,8-dimethoxy-1,4-naphthoquinone

According to the same procedure as Example 32, 2-(1-hydroxytridecyl)-1,4,5,8-tetramethoxynaphthalene was used to obtain 3.0 g of the title compound as a yellow precipitate.

Yield: 71.5%

TLC (n-hexane:ethylacetate=1:2): Rf=0.35

Melting Point: 91.7°–93.2° C.

$^1$H-NMR (CDCl$_3$, δ ppm): 7.30(s, 2H), 6.78(d, J=1.1 Hz, 1H), 4.76(m, 1H), 3.95(s, 6H), 2.89(d, J=5.0 Hz, 1H), 1.63(m, 2H), 1.50–1.15(m, 20H), 0.88(t, J=6.1 Hz, 3H)

$^{13}$C-NMR (CDCl$_3$, δ ppm): 185.3, 184.9, 153.8, 153.4, 151.3, 133.4, 121.1, 120.8, 120.4, 120.1, 69.0, 56.8, 56.7, 36.5, 31.8, 29.5, 29.4(5C), 29.2, 25.8, 22.6, 14.0

IR: 3440, 2820, 1650, 1470

MASS: 416(M$^+$, 28), 401(100), 400(51), 387(37), 247 (48), 233(11), 219(10), 191(2), 57(2)

EXAMPLE 37

Preparation of 2-(1-hydroxy-3-methyl-2-butenyl)-5,8-dimethoxy-1,4-naphthoquinone According to the same procedure as Example 32, 2-(1-hydroxy-3-methyl-2-butenyl)-1,4,5,8-tetramethoxynaphthalene was used to obtain the title compound as a yellow precipitate.

Yield: 48%

TLC (n-hexane:ethylacetate=1:2): Rf=0.12

Melting Point: 168°–170° C.

$^1$H-NMR (CDCl$_3$, δ ppm): 7.29(s, 2H), 7.00–6.50(m, 3H), 3.94(s, 6H), 2.27(br.s, 1H), 1.41(s, 6H)

$^{13}$C-NMR (CDCl$_3$, δ ppm): 184.8, 184.5, 153.6, 153.1, 146.6, 143.7, 131.1, 121.6, 121.0, 120.1, 119.6, 118.4, 71.1, 56.7, 57.0, 29.4(2C)

IR: 2470, 2970, 1650, 1475

MASS: 302(M$^+$, 100) 260(31) 255(56) 245(26) 58(20)

EXAMPLE 38

Preparation of 2-(1-acetoxy-4-methylpentyl)-5,8-dimethoxy-1,4-naphthoquinone

According to the same procedure as Example 32, 2-(1-acetoxy-4-methylpentyl)-1,4,5,8-tetramethoxynaphthalene was used to obtain the title compound as a pale yellow precipitate.

Yield: 45%

TLC (n-hexane:ethylacetate=1:2): Rf=0.13

Melting Point: 125.5°–127.0° C.

$^1$H-NMR (CDCl$_3$, δ ppm): 7.31(s, 2H), 6.65(s, 1H), 3.95(s, 6H), 2.11(s, 3H), 2.00–1.10(m, 5H), 0.87(d, J=6.3 Hz, 6H)

$^{13}$C-NMR (CDCl$_3$, δ ppm): 184.7, 183.5, 169.8, 154.1, 153.6, 149.5, 132.9, 121.2, 121.1, 120.6, 120.4, 70.0, 56.9, 56.8, 34.4, 32.5, 27.8, 22.6, 22.3, 20.9

IR: 2950, 1740, 1650, 1470

EXAMPLE 39

Preparation of 2-(1-ethoxy-4-methylpentyl)-5,8-dimethoxy-1,4-naphthoquinone 600 mg (3.4 mmole) of 2-(1-ethoxy-4-methylpentyl)-1,4,5,8-tetramethoxynaphthalene was dissolved in 25 ml of acetonitrile and then a solution of 8.6 g (17 mmole) of cerium (IV) ammonium nitrate dissolved in 25 ml of distilled water was added dropwise thereto over 30 minutes through a dropping funnel in a cooling bath (0°–5° C.). The reaction mixture was stirred at normal temperature for 2 hours. After adding 60 mg of distilled water thereto, the reaction mixture was extracted twice with dichloromethane solvent, dried over anhydrous magnesium sulfate and then filtered through filter paper. The resulting filtrate was concentrated under reduced pressure to obtain a crude product. The crude product was purified by silica gel column chromatography (silica gel 4.0×15 cm) using the solvent condition which increases the amount of ethylacetate so that the n-hexane/ethylacetate ratio can vary from 10:1 to 1:1, to obtain 300 mg of the title compound as a yellow precipitate.

Yield: 27%

TLC (n-hexane:ethylacetate=2:1): Rf=0.10

$^1$H-NMR (CDCl$_3$, δ ppm): 7.33(s, 2H), 6.81(d, J=1.0 Hz, 1H), 4.52(m, 1H), 3.96(s, 6H), 3.44(m, 2H), 1.90–1.10(m, 5H), 1.20(t, J=7.1 Hz, 3H), 0.87(d, J=6.0 Hz, 3H)

$^{13}$C-NMR (CDCl$_3$, δ ppm): 184.9, 184.8, 153.6, 153.3, 150.8, 133.1, 121.2, 121.0, 120.3, 119.9, 74.9, 64.9, 56.7, 56.6, 34.5, 33.9, 27.7, 22.4, 22.2, 15.1

IR: 2950, 1650, 1470, 1270

MASS: 346(M$^+$, 31), 317(100), 302(14), 257(14), 243(11), 219(11), 149(5), 86(14), 84(18)

EXAMPLE 40

Preparation of 2-[1-(3-methylbutoxy)-4-methylpentyl]-5,8-dimethoxy-1,4-naphthoquinone According to the same procedure as Example 39, 2-[1-(4-methylbutoxy)-4-methylpentyl]-1,4,5,8-tetramethoxynaphthalene was used to obtain 476 mg of the title compound as a reddish brown precipitate.

Yield: 36%

TLC (n-hexane:ethylacetate=2:1): Rf=0.21

Melting Point: 90.0°–91.7° C.

$^1$H-NMR (CDCl$_3$, δ ppm): 7.33(s, 2H), 6.82(s, 1H), 4.51(m, 1H), 3.97(s, 3H), 3.42(m, 2H), 1.90–1.10(m, 8H), 0.89(d, J=6.3 Hz, 6H), 0.87 (d, J=6.3 Hz, 6H)

$^{13}$C-NMR (CDCl$_3$, δ ppm): 184.9, 184.6, 153.7, 152.3, 150.9, 133.2, 121.3, 121.1, 120.3, 119.9, 75.1, 68.1, 56.7, 56.6, 38.5, 34.5, 33.9, 27.7, 24.8, 22.5, 22.4, 22.3, 22.2

IR: 2950, 1650, 1470, 1275

MASS: 388(M$^+$, 20) 303(15) 247(3) 203(6), 131(3), 115(4), 71(10), 55(15), 43(100)

EXAMPLE 41

Preparation of 2-(1-pentyloxy-4-methylpentyl)-5,8-dimethoxy-1,4-naphthoquinone

According to the same procedure as Example 39, 2-(1-heptyloxy-4-methylpentyl)-1,4,5,8-tetramethoxynaphthalene was used to obtain 597 mg of the title compound as a yellow precipitate.

Yield: 46%

TLC (n-hexane:ethylacetate=2:1): Rf=0.19

Melting Point: 78.9°–80.3° C.

$^1$H-NMR (CDCl$_3$, δ ppm): 7.33(s, 2H), 6.81(s, 1H), 4.47(m, 1H), 3.96(s, 6H), 3.34(m, 2H), 1.80–1.15(m, 11H), 0.95–0.75(m, 9H)

$^{13}$C-NMR (CDCl$_3$, δ ppm): 184.9, 184.8, 153.6, 153.3, 150.8, 133.2, 121.2, 121.1, 120.3, 119.9, 75.1, 69.8, 56.7, 56.6, 34.5, 33.9, 29.3, 28.1, 27.7, 22.5, 22.2, 22.1,

IR: 2950, 2650, 1475

EXAMPLE 42

Preparation of 2-(1-heptyloxy-4-methylpentyl)-5,8-dimethoxy-1,4-naphthoquinone

According to the same procedure as Example 39, 2-(1-heptyloxy-4-methylpentyl]-1,4,5,8-tetramethoxynaphthalene was used to obtain 515 mg of the title compound as a yellowish red oil.

Yield: 37%

TLC (n-hexane:ethylacetate=2:1): Rf=0.15

$^1$H-NMR (CDCl$_3$, δ ppm): 7.34(s, 2H), 6.83(s, 1H), 4.52(m, 1H), 5.98(s, 6H), 3.41(m, 2H), 1.80–1.15(m, 15H), 0.95–0.75(m, 9H)

$^{13}$C-NMR (CDCl$_3$, δ ppm): 185.0(2C), 153.7, 153.3, 150.9, 133.2, 121.3, 121.1, 120.3, 119.9, 75.1, 69.8, 56.7, 56.6, 34.6, 33.9, 31.6, 29.7, 28.9, 27.7, 25.9, 22.6, 22.4, 22.2, 13.9

IR: 2950, 1650, 1475

EXAMPLE 43

Preparation of 2-(1-dodecyloxy-4-methylpentyl)-5,8-dimethoxy-1,4-naphthoquinone

According to the same procedure as Example 39, 2-(1-dodecyloxy-4-methylpentyl)-1,4,5,8-tetramethoxynaphthalene was used to obtain 360 mg of the title compound as a yellowish red oil.

Yield: 54%

TLC (n-hexane:ethylacetate=2:1): Rf=0.22

$^1$H-NMR (CDCl$_3$, δ ppm): 6.96(s, 1H), 6.82(s, 2H), 4.83(m, 1H), 3.93(s, 6H), 3.89(s, 3H), 3.75(s, 3H), 3.30(t, J=6.3 Hz, 2H), 1.90–1.10(m, 25H), 1.90–1.75(m, 9H)

$^{13}$C-NMR (CDCl$_3$, δ ppm): 153.5, 151.5, 150.3, 147.3, 133.6, 124.0, 120.2, 108.4, 107.7, 105.7, 75.5, 69.1, 62.5, 57.9, 56.9(2C), 35.8, 35.7, 35.3, 31.9, 29.9, 29.6, 29.4, 29.3, 28.0, 26.4, 22.6, 22.5, 14.0

IR: 2925, 1600, 1460, 1320

EXAMPLE 44

Preparation of 2-(1-hydroxypentyl)-5,8-dihydroxy-1,4-naphthoquinone 1.7 g (5.6 mmole) of the compound prepared in Example 32 and 4.16 g (33.5 mmole) of silver oxide (II) were dissolved in 30 ml of acetone and then 40 ml of 40% aqueous HNO$_3$ solution was added dropwise thereto over 10 minutes through a dropping funnel in a cooling bath. The reaction mixture was stirred at normal temperature for 3 hours, extracted with dichloromethane, dried over anhydrous magnesium sulfate and then filtered through filter paper. The filtrate was concentrated under reduced pressure to obtain a crude product. The crude product was purified by silica gel column chromatography (silica gel 2.5×15 cm) using the solvent condition which increases the amount of ethylacetate so that the n-hexane/ethylacetate ratio can vary from 20:1 to 4:1, to obtain 540 mg of the title compound as a red precipitate.

Yield: 35%

TLC (n-hexane:ethylacetate=4:1): Rf=0.29

Melting Point: 99.0°–102.0° C.

$^1$H-NMR (CDCl$_3$, δ ppm): 12.55(s, 1H), 12.43(s, 1H), 7.17(s, 2H), 7.11(d, J=1.0 Hz, 1H), 4.90(m, 1H), 2.48(s, 1H), 1.75(m, 2H), 1.60–1.15(m, 4H), 0.92(t, J=6.0 Hz, 3H)

$^{13}$C-NMR (CDCl$_3$, δ ppm): 180.2, 179.5, 165.9, 165.2, 152.0, 132.4, 32.1, 132.0, 112.0, 111.5, 68.9, 36.5, 27.7, 22.4, 13.9

IR: 2925, 1605, 1450, 1200

MASS: 276(M$^+$, 66), 275(24), 229(10), 220(17), 219(100), 192(7), 111(3)

EXAMPLE 45

Preparation of 2-(1-hydroxyhexyl)-5,8-dihydroxy-1,4-naphthoquinone

According to the same procedure as Example 44, the compound prepared in Example 33 was used to obtain 674 mg of the title compound as a red precipitate.

Yield: 40%

TLC (n-hexane:ethylacetate=4:1): Rf=0.30

Melting Point: 99.7°–101.0° C.

$^1$H-NMR (CDCl$_3$, δ ppm): 12.53(s, 1H), 12.41(s, 1H), 7.15(s, 2H), 7.10(d, J=1.0 Hz, 1H), 4.88(m, 1H), 2.69(br.s, 1H), 1.73 (m, 2H), 1.55–1.10(m, 6H), 0.89(t, J=6.0 Hz, 3H)

$^{13}$C-NMR (CDCl$_3$, δ ppm): 180.1, 179.4, 165.8, 165.2, 152.1, 132.3, 132.0, 131.9, 112.0, 111.4, 68.7, 36.7, 31.5, 25.3, 22.5, 14.0

IR: 3450, 2925, 1600, 1450

MASS: 290(M$^+$, 6), 229(8), 219(83), 191(11), 167(28), 149(100), 107(5), 71(21), 57(28)

EXAMPLE 46

Preparation of 2-(1-hydroxyoctyl)-5,8-dihydroxy-1,4-naphthoquinone

According to the same procedure as Example 44, the compound prepared in Example 34 was used to obtain 716 mg of the title compound as a red precipitate.

Yield: 40%

TLC (n-hexane:ethylacetate=2:1): Rf=0.51

Melting Point: 62.5°–63.7° C.

$^1$H-NMR (CDCl$_3$, δ ppm): 12.54(s, 1H), 12.42(s, 1H), 7.16(s, 2H), 7.10(d, J=0.9 Hz, 1H), 4.88(m, 1H), 2.64(m, 1H), 1.71(m, 2H), 1.70–1.10(m, 10H), 0.87(t, J=6.0 Hz, 3H)

$^{13}$C-NMR (CDCl$_3$, δ ppm): 180.2, 179.5, 165.8, 165.1, 152.1, 132.3, 132.1, 131.9, 112.0, 111.4, 68.7, 36.8, 31.7, 29.3, 29.1, 25.7, 22.6, 14.0

IR: 3450, 2925, 1600, 1450

MASS: 318(M$^+$, 22), 300(21), 229(10), 219 (100), 205 (11), 137(3), 97(5), 83(6)

EXAMPLE 47

Preparation of 2-(1-hydroxydecyl)-5,8-dihydroxy-1,4-naphthoquinone

According to the same procedure as Example 44, the compound prepared in Example 35 was used to obtain 1.05 g of the title compound as a red precipitate.

Yield: 55%

TLC (n-hexane:ethylacetate=4:1): Rf=0.38

Melting Point: 74.1°–75.2° C.

$^1$H-NMR (CDCl$_3$, δ ppm): 12.57(s, 1H), 12.45(s, 1H), 7.18(s, 2H), 7.12(d, J=1.0 Hz, 1H), 4.88(m, 1H), 2.41(br.s, 1H), 1.70(m, 2H), 1.60–1.00(m, 14H), 0.87(t, J=6.0 Hz, 3H)

$^{13}$C-NMR (CDCl$_3$, δ ppm): 180.3, 179.7, 165.8, 165.1, 152.0, 132.4, 132.2, 132.0, 112.0, 111.5, 68.9, 36.8, 31.8, 29.5, 29.3(2C), 29.2, 25.7, 22.6, 14.1

IR: 3450, 2920, 1605, 1450

MASS: 346(M$^+$, 29), 328(16), 234(5), 219(100), 205 (27), 192(27), 149(5), 85(2)

EXAMPLE 48

Preparation of 2-(1-hydroxytridecyl)-5,8-dihydroxy-1,4-naphthoquinone

According to the same procedure as Example 44, the compound prepared in Example 36 was used to obtain 0.73 g of the title compound as a red precipitate.

Yield: 34%

TLC (n-hexane:ethylacetate=4:1): Rf=0.41

Melting Point: 77.5°–79.2° C.

$^1$H-NMR (CDCl$_3$, δ ppm): 12.55(s, 1H), 12.44(s, 1H), 7.17(s, 2H), 7.11(d, J=1.1 Hz, 1H), 4.85(m, 1H), 2.50(d, J=5.4 Hz, 1H), 1.90–1.10(m, 22H), 0.87(t, J=6.0 Hz, 3H)

$^{13}$C-NMR (CDCl$_3$, δ ppm): 180.4, 179.6, 165.8, 165.2, 152.0, 132.4, 132.1, 112.0, 111.5, 68.9, 36.8, 31.9, 29.6, 29.5(6C), 25.7, 22.7, 14.1

IR: 2910, 1605, 1450, 1200

MASS: 388(M$^+$, 34) 370(23) 220(29), 219(100), 205 (9), 92(10), 71(11)

EXAMPLE 49

Preparation of 2-(1-hydroxy-3-methylbut-2-enyl)-5,8-dihydroxy-1,4-naphthoquinone According to the same procedure as Example 44, the compound prepared in Example 37 was used to obtain the title compound as a yellow precipitate.

Yield: 30%

TLC (n-hexane:ethylacetate=2:1): Rf=0.25

Melting Point: 154.5°–156.1° C.

$^1$H-NMR (CDCl$_3$, δ ppm): 12.54(s, 1H), 12.10(s, 1H), 7.15(s, 2H), 7.10–6.50(m, 3H), 1.43(s, 6H)

IR: 2970, 1650, 1475

EXAMPLE 50

Preparation of 2-(1-acetoxy-4-methylpentyl)-5,8-dihydroxy-1,4-naphthoquinone

According to the same procedure as Example 44, the compound prepared in Example 38 was used to obtain the title compound as a reddish brown precipitate.

Yield: 45%

TLC (n-hexane:ethylacetate=5:1): Rf=0.32

Melting Point: 105.0°–106.8° C.

$^1$H-NMR (CDCl$_3$, δ ppm): 12.56(s, 1H), 12.41(s, 1H), 7.16(s, 2H), 6.99(d, J=0.9 Hz, 1H), 5.98(m, 1H), 2.14(s, 3H), 2.00–1.10(m, 5H), 0.88(d, J=6.2 Hz, 6H)

$^{13}$C-NMR (CDCl$_3$, δ ppm): 177.9, 176.4, 169.8, 167.8, 167.3, 132.9, 132.8, 131.0, 111.9, 111.6, 69.6, 34.3, 32.5, 27.7, 22.6, 22.2, 20.9

IR: 2950, 1740, 1610, 1450

EXAMPLE 51

Preparation of 2-(1-ethoxy-4-methylpentyl)-5,8-dihydroxy-1,4-naphthoquinone 170 mg (0.5 mmole) of the compound prepared in Example 39 and 310 mg (2.5 mmole) of silver oxide (II) were dissolved in 20 ml of acetone and then 3.6 ml of 40% aqueous HNO$_3$ solution was added dropwise thereto over 10 minutes through a dropping funnel in a cooling bath. The reaction mixture was stirred at normal temperature for 3 hours, extracted with dichloromethane, dried over anhydrous magnesium sulfate and then filtered through filter paper. The filtrate was concentrated under reduced pressure to obtain a crude product. The crude product was purified by silica gel column chromatography (silica gel 1.5×10 cm) using the solvent condition which increases the amount of ethylacetate so that the n-hexane/ethylacetate ratio can vary from 20:1 to 4:1, to obtain 48 mg of the title compound as a red precipitate.

Yield: 30%

TLC (n-hexane:ethylacetate=5:1): Rf=0.54

Melting Point: 59.5°–61.8° C.

$^1$H-NMR (CDCl$_3$, δ ppm): 12.59(s, 1H), 12.50(s, 1H), 7.18(s, 2H), 7.14(d, J=1.0 Hz), 4.58(m, 1H), 3.46(q, J=7.3 Hz, 2H), 1.90–1.10(m, 8H), 0.89(d, J=6.3 Hz, 6H)

$^{13}$C-NMR (CDCl$_3$, δ ppm): 179.7, 179.0, 166.5, 166.0, 151.6, 132.5, 131.9, 112.1, 111.7, 75.1, 65.4, 34.6, 34.2, 27.9, 22.7, 22.4, 15.3

IR: 2950, 1600, 1450, 1340

MASS: 318(M$^+$, 42), 289(21), 274(22), 248(44), 247(100), 229(49), 219(100), 204(21), 149(12), 69(17)

EXAMPLE 52

Preparation of 2-[1-(3-methylbutoxy)-4-methylpentyl]-5,8-dihydroxy-1,4-naphthoquinone According to the same procedure as Example 51, the compound prepared in Example 40 was used to obtain 82.6 mg of the title compound as a red precipitate.

Yield: 46%

TLC (n-hexane:ethylacetate=5:1): Rf=0.53

Melting Point: 64.0°–65.2° C.

$^1$H-NMR (CDCl$_3$, δ ppm): 12.58(s, 1H), 12.49(s, 1H), 7.17–7.13 (m, 3H), 4.59(m, 1H), 3.40(m, 2H), 1.90–1.10(m, 8H), 0.89(d, J=6.0 Hz, 12H) 7.17–7.13 (m, 3H), $^{13}$C-NMR (CDCl$_3$, δ ppm): 179.8, 179.1, 166.3, 165.7, 151.6, 132.4, 132.0, 131.9, 112.0, 111.6, 75.2, 68.4, 38.7, 34.5, 34.0, 27.8, 25.0, 22.7, 22.6, 22.5, 22.3

IR: 2750, 1610, 1450, 1340

MASS: 360(M$^+$, 5) 289(21) 219(54) 205(12) 149(6), 137(7), 99(11), 97(30), 71(76), 43(100)

EXAMPLE 53

Preparation of 2-(1-pentyloxy-4-methylpentyl)-5,8-dihydroxy-1,4-naphthoquinone

According to the same procedure as Example 51, the compound prepared in Example 41 was used to obtain 62 mg of the title compound as a red precipitate.

Yield: 35%

TLC (n-hexane:ethylacetate=5:1): Rf=0.54

Melting Point: 68.5°–69.8° C.

$^1$H-NMR (CDCl$_3$, δ ppm): 12.60(s, 1H), 12.50(s, 1H), 7.18(s, 1H), 7.13(d, J=9.0 Hz, 1H), 4.60(m, 1H), 3.36(m, 2H), 1.80(m, 11H), 0.95–0.75(m, 9H)

$^{13}$C-NMR (CDCl$_3$, δ ppm): 179.8, 179.1, 166.3, 165.8, 151.6, 132.4, 132.1, 132.0, 112.1, 111.6, 75.5, 70.1, 34.5, 34.1, 29.5, 28.3, 27.8, 22.6, 22.4, 22.3, 14.0

IR: 2950, 1600, 1450

EXAMPLE 54

Preparation of 2-(1-heptyloxy-4-methylpentyl)-5,8-dihydroxy-1,4-naphthoquinone

According to the same procedure as Example 51, the compound prepared in Example 42 was used to obtain 119 mg of the title compound as a red precipitate.

Yield: 37%

TLC (n-hexane:ethylacetate=5:1): Rf=0.52

Melting Point: 40.2°–42.7° C.

$^1$H-NMR (CDCl$_3$, δ ppm): 12.60(s, 1H), 12.50(s, 1H), 7.18(s, 2H), 7.13(d, J=0.9 Hz, 1H), 4.56(m, 1H), 3.39(m, 2H), 1.80–1.10(m, 15H), 0.95–0.75(m, 9H)

$^{13}$C-NMR (CDCl$_3$, δ ppm): 179.8, 179.1, 166.4, 165.8, 151.7, 132.4, 132.1, 122.0, 112.1, 111.6, 75.2, 70.2, 34.6, 34.1, 31.8, 29.9, 29.1, 27.9, 26.1, 22.7, 22.6, 22.3, 14.0,

IR: 2950, 1605, 1450

EXAMPLE 55

Preparation of 2-(1-dodecyloxy-4-methylpentyl)-5,8-dihydroxy-1,4-naphthoquinone

According to the same procedure as Example 51, the compound prepared in Example 43 was used to obtain 105 mg of the title compound as a red precipitate.

Yield: 46%

TLC (n-hexane:ethylacetate=5:1): Rf=0.57

Melting point: 48.8°–51.2° C.

$^1$H-NMR (CDCl$_3$, δ ppm): 12.58(s, 1H), 12.48(s, 1H), 7.16(s, 2H), 7.13 (d, J=0.9 Hz, 1H), 4.56(m, 1H), 3.36(m, 2H), 1.90–1.00(m, 25H), 0.95–0.70(m, 9H)

$^{13}$C-NMR (CDCl$_3$, δ ppm): 179.8, 179.1, 166.3, 165.7, 151.7, 132.4, 132.0(C), 112.1, 111.6, 75.2, 70.2, 34.6, 34.3, 34.1, 31.9, 29.9, 29.6, 29.4, 29.3, 27.9, 26.2, 21.9, 14.0, 22.6, 22.4, 22.3

IR: 2925, 1605, 1450, 1340

MASS: 458(M$^+$, 15), 387(70), 274(37), 229(14), 219(100), 149(9), 127(12), 113(8), 85(14), 71(20), 57(20)

EXAMPLE 56

Preparation of 2-(1-acetoxyhexyl)-5,8-dihydroxy-1,4-naphthoquinone

In a 25 ml two-neck flask 1 mmole of the compound prepared in Example 45, 266 mg (1.1 mole) of DCC and 30 mg (0.25 mmole) of 4-dimethylaminopyridine were introduced and then 3 ml of dry dichloromethane was added thereto. After adding 60 mg (1 mmole) of acetic acid at 0° C. under nitrogen gas, the reaction mixture was stirred for 30 minutes and then subsequently stirred at normal temperature for a further 3 hours. To the reaction mixture was added 20 ml of n-hexane. The mixture was stirred for a further 10 minutes and then filtered to remove the insoluble materials. The filtrate was concentrated under reduced pressure to obtain a crude product. The crude product was purified by silica gel column chromatography (silica gel 2.5×20 cm) using the solvent condition which increases the amount of ethylacetate so that the n-hexane/ethylacetate ratio can vary from 20:1 to 5:1, to obtain 256 mg of the title compound as a reddish brown precipitate.

Yield: 77%

TLC (n-hexane:ethylacetate=2:1): Rf=0.39

Melting Point: 97.0°–98.4° C.

$^1$H-NMR (CDCl$_3$, δ ppm): 12.55(s, 1H), 12.40(s, 1H), 7.17(s, 2H), 6.99(d, J=1.0 Hz, 1H), 6.00(m, 1H), 2.15(s, 3H), 2.00–1.20(m, 9H), 0.82(t, J=6.3 Hz, 3H)

$^{13}$C-NMR (CDCl$_3$, δ ppm): 178.1, 176.5, 169.8, 167.5, 167.0, 148.9, 132.9, 132.7, 131.0, 111.8, 111.5, 69.4, 34.5, 31.3, 25.0, 22.4, 20.9, 13.9

IR: 2950, 1740, 1610, 1455

EXAMPLE 57

Preparation of 2-(1-hexanoyloxyhexyl)-5,8-dihydroxy-1,4-naphthoquinone

According to the same procedure as Example 56, except that n-hexanoic acid is used instead of acetic acid used in Example 56, 258 mg of the title compound was obtained as a reddish brown precipitate.

Yield: 73%

TLC (n-hexane:ethylacetate=5:1): Rf=0.43

$^1$H-NMR (CDCl$_3$, δ ppm): 12.55(s, 1H), 12.39(s, 1H), 7.16(s, 2H), 6.98 (d, J=1.0 Hz, 1H), 6.01(m, 1H), 2.41(t, J=7.3 Hz, 2H), 1.95–1.10(m, 14H), 1.00–0.80(m, 6H)

$^{13}$C-NMR (CDCl$_3$, δ ppm): 178.2, 176.6, 172.6, 167.3, 166.8, 149.1, 132.7, 132.6, 13.0, 122.8, 111.5, 69.0, 34.5, 34.2, 31.2, 25.0, 24.6, 22.3, 22.2, 13.8, 13.7

IR: 2950, 1740, 1610, 1450

EXAMPLE 58

Preparation of 2-(1-octanoyloxyhexyl)-5,8-dihydroxy-1,4-naphthoquinone

According to the same procedure as Example 56, except that n-octanoic acid is used instead of acetic acid used in Example 56, 338 mg of the title compound was obtained as a reddish brown precipitate.

Yield: 78%

TLC (n-hexane:ethylacetate=5:1): Rf=0.45

$^1$H-NMR (CDCl$_3$, δ ppm): 12.56(s, 1H), 12.41(s, 1H), 7.17(s, 2H), 6.98(d, J=1.0 Hz, 1H), 6.01(m, 1H), 2.41(t, J=7.3 Hz, 2H), 1.95–1.10(m, 18H), 1.00–0.80(m, 6H)

$^{13}$C-NMR (CDCl$_3$, δ ppm): 178.2, 176.6, 172.7, 167.5, 167.0, 149.2, 132.8, 132.7, 131.0, 111.9, 111.6, 69.1, 34.5, 34.3, 31.6, 31.3, 29.1, 28.9, 25.0, 24.9, 22.6, 22.4, 14.0, 13.9

IR: 2925, 1740, 1610, 1450

EXAMPLE 59

Preparation of 2-[1-(3-trans-hexenoyloxy)-hexyl]-5,8-dihydroxy-1,4-naphthoquinone According to the same procedure as Example 56, except that 3-trans-hexenoic acid is used instead of acetic acid used in Example 56, 167 mg of the title compound was obtained as a reddish brown precipitate.

Yield: 43%

TLC (n-hexane:ethylacetate=5:1): Rf=0.45

$^1$H-NMR (CDCl$_3$, δ ppm): 12.56(s, 1H), 12.41(s, 1H), 7.17(s, 2H), 6.97(d, J=0.9 Hz, 1H), 6.00(m, 1H), 5.63(m, 2H), 3.13(d, J=6.0 Hz, 2H), 2.25–0.85(m, 17H)

$^{13}$C-NMR (CDCl$_3$, δ ppm): 178.1, 176.6, 171.0, 167.6, 167.1, 149.0, 137.1, 132.9, 132.7, 131.1, 119.9, 111.9, 111.6, 69.4, 38.0, 34.5, 31.3, 25.5, 25.0, 22.4, 13.9, 13.4

IR: 2950, 1740, 1610, 1450

EXAMPLE 60

Preparation of 2-(1-acetoxy-4-methylpentyl)-5,8-dihydroxy-1,4-naphthoquinone

According to the same procedure as Example 56, except that the known compound 2-(1-hydroxy-4-methylpentyl)-5,8-dihydroxy-1,4-naphthoquinone is used as the starting compound, 298 mg of the title compound was obtained as a reddish brown precipitate.

Yield: 90%

TLC (n-hexane:ethylacetate=5:1): Rf=0.32

Melting Point: 105.0°–106.8° C.

$^1$H-NMR (CDCl$_3$, δ ppm): 12.56(s, 1H), 12.41(s, 1H), 7.16(s, 2H), 6.99(d, J=0.9 Hz, 1H), 5.98(m, 1H), 2.14(s, 3H), 2.00–1.10(m, 5H), 0.88(d, J=6.2 Hz, 6H)

$^{13}$C-NMR (CDCl$_3$, δ ppm): 177.9, 176.4, 169.8, 167.8, 167.3, 148.9, 122.9, 132.8, 131.0, 111.9, 111.6, 69.6, 34.3, 32.5, 27.7, 22.6, 22.2, 20.9

IR: 2950, 1740, 1610, 1450

EXAMPLE 61

Preparation of 2-(1-hexanoyl-4-methylpentyl)-5,8-dihydroxy-1,4-naphthoquinone

According to the same procedure as Example 56, except that n-hexanoic acid is used instead of acetic acid used in Example 56, 349 mg of the title compound was obtained as a reddish brown precipitate.

Yield: 90%

TLC (n-hexane:ethylacetate=4:1): Rf=0.54

Melting Point: 60.7°–62.3° C.

$^1$H-NMR (CDCl$_3$, δ ppm): 12.56(s, 1H), 12.40(s, 1H), 7.16(s, 2H), 6.98(d, J=1.0 Hz, 1H), 5.99(m, 1H), 2.41(t, J=1.0 Hz, 1H), 5.99(m, 1H), 2.41(t, J=7.5 Hz, 2H), 2.00–1.10(m, 11H), 0.95–0.75(m, 9H)

$^{13}$C-NMR (CDCl$_3$, δ ppm): 178.1, 176.6, 172.6, 167.5, 166.9, 149.1, 132.8, 132.6, 131.0, 111.8, 111.5, 69.2, 34.2, 32.5, 31.2, 27.7, 24.6, 22.6, 22.3, 22.2, 13.8

IR: 2950, 1740, 1610

EXAMPLE 62

Preparation of 2-(1-octanoyloxy-4-methylpentyl)-5,8-dihydroxy-1,4-naphthoquinone According to the same procedure as Example 56, except that n-octanoic acid is used instead of acetic acid used in Example 56, 290 mg of the title compound was obtained as a reddish brown precipitate.

Yield: 70%

TLC (n-hexane:ethylacetate=4:1): Rf=0.55

Melting Point: 39.6°–42.2° C.

$^1$H-NMR (CDCl$_3$, δ ppm): 12.57(s, 1H), 12.41(s, 1H), 7.17(s, 2H), 6.98(d, J=0.9 Hz, 1H), 5.99(m, 1H), 2.41(t, J=6.5 Hz, 2H), 2.00–1.10(m, 15H), 0.95–0.75(m, 9H)

$^{13}$C-NMR (CDCl$_3$, δ ppm): 178.1, 176.6, 172.7, 167.6, 167.0, 149.2, 132.7, 132.6, 131.1, 111.9, 111.6, 69.3, 34.3, 32.5, 31.6, 29.1, 28.9, 27.7, 24.9, 22.6, 22.2, 22.1, 14.0

IR: 2950, 1740, 1605, 1450

EXAMPLE 63

Preparation of 2-[1-(3-trans-hexenoyloxy)-4-methylpentyl]-5,8-dihydroxy-1,4-naphthoquinone According to the same procedure as Example 56, except that 3-trans-hexenoic acid is used instead of acetic acid used in Example 56, 292 mg of the title compound was obtained as a reddish brown precipitate.

Yield: 75%

TLC (n-hexane:ethylacetate=4:1): Rf=0.50

$^1$H-NMR (CDCl$_3$, δ ppm): 12.56(s, 1H), 12.41(s, 1H), 7.17(s, 2H), 6.98(d, J=1.0 Hz, 1H), 5.98(m, 1H), 5.66(m, 2H), 3.13(d, J=6.0 Hz, 2H), 2.25–1.20(m, 7H), 1.01(t, J=7.3 Hz, 3H), 0.88(d, J=6.3 Hz, 6H)

$^{13}$C-NMR (CDCl$_3$, δ ppm): 178.0, 176.4, 171.0, 167.6, 167.1, 148.9, 137.1, 132.9, 132.7, 131.0, 119.9, 111.8, 111.6, 69.5, 38.0, 34.2, 32.4, 27.7, 25.4, 22.6, 22.2, 13.3

IR: 2950, 1740, 1610, 1450

EXAMPLE 64

Preparation of 2-(1-acetoxydecyl)-5,8-dihydroxy-1,4-naphthoquinone

According to the same procedure as Example 56, except that the compound prepared in Example 47 is used as the starting compound, 346 mg of the title compound was obtained as a reddish brown precipitate.

Yield: 89%

TLC (n-hexane:ethylacetate=5:1): Rf=0.41

$^1$H-NMR (CDCl$_3$, δ ppm): 12.55(s, 1H), 12.40(s, 1H), 7.17(s, 2H), 6.99(d, J=0.9 Hz, 1H), 6.00(m, 1H), 2.15(s, 3H), 1.95–1.10(m, 16H), 0.87(t, J=6.3 Hz, 3H)

$^{13}$C-NMR (CDCl$_3$, δ ppm): 178.1, 176.5, 169.8, 167.5, 167.0, 148.9, 132.8, 132.6, 131.0, 131.0, 111.8, 111.5, 69.4, 34.5, 31.8, 29.4, 29.3(2C), 29.1, 25.3, 22.6, 20.9, 14.0

IR: 2925, 1745, 1610, 1455

EXAMPLE 65

Preparation of 2-(1-hexanoyloxydecyl)-5,8-dihydroxy-1,4-naphthoquinone

According to the same procedure as Example 64, except that n-hexanoic acid is used instead of acetic acid used in Example 64, 269 mg of the title compound was obtained as a reddish brown precipitate.

Yield: 61%

TLC (n-hexane:ethylacetate=5:1): Rf=0.57

$^1$H-NMR (CDCl$_3$, δ ppm): 12.56(s, 1H), 12.40(s, 1H), 7.17(s, 2H), 6.98(d, J=1.0 Hz, 1H), 6.00(m, 1H), 2.40(t, J=7.0 Hz, 2H), 1.85–1.10(m, 26H), 1.00–0.75(m, 6H)

$^{13}$C-NMR (CDCl$_3$, δ ppm): 178.2, 176.6, 172.6, 167.5, 166.9, 149.2, 132.8, 132.6, 131.0, 111.8, 111.5, 69.1, 34.5, 34.2, 31.8, 31.2, 29.4, 29.3, 29.2, 29.1, 25.3, 24.6, 22.6, 22.3, 14.0, 13.8

IR: 2950, 1740, 1605

EXAMPLE 66

Preparation of 2-(1-octanoyloxydecyl)-5,8-dihydroxy-1,4-naphthoquinone

According to the same procedure as Example 64, except that n-octanoic acid is used instead of acetic acid used in Example 64, 327 mg of the title compound was obtained as a reddish brown precipitate.

Yield: 69%

TLC (n-hexane:ethylacetate=5:1): Rf=0.60

Melting Point: 52.7°–53.7° C.

$^1$H-NMR (CDCl$_3$, δ ppm): 12.56(s, 1H), 12.40(s, 1H), 7.16(s, 1H), 6.98(m, 1H), 2.41(t, J=7.0 Hz, 2H), 1.95–1.10 (m, 26H), 1.00–0.80(m, 6H)

$^{13}$C-NMR (CDCl$_3$, δ ppm): 178.3, 176.7, 172.6, 167.4, 166.9, 149.2, 132.8, 132.6, 131.1, 111.8, 111.6, 69.1, 34.6, 34.3, 31.8, 29.4, 29.3, 29.3, 29.2, 29.0, 28.9, 25.4, 24.9, 22.6, 22.5, 14.1, 14.0

IR: 2950, 1740, 1605, 1450

EXAMPLE 67

Preparation of 2-[1-(3-trans-hexenoyloxy)-decyl]-5,8-dihydroxy-1,4-naphthoquinone According to the same procedure as Example 64, except that 3-trans-hexenoic acid is used instead of acetic acid used in Example 64, 184 mg of the title compound was obtained as a reddish brown precipitate.

Yield: 42%

TLC (n-hexane:ethylacetate=4:1): Rf=0.42

Melting Point: 95.3°–97.3° C.

$^1$H-NMR (CDCl$_3$, δ ppm): 12.56(s, 1H), 12.41(s, 1H), 7.17(s, 2H), 6.97(d, J=1.0 Hz, 1H), 5.99(m, 1H), 5.71(m, 2H), 3.11(d, J=6.0 Hz, 2H), 2.25–0.80 (m, 24H)

$^{13}$C-NMR (CDCl$_3$, δ ppm): 178.1, 176.6, 171.0, 167.5, 167.0, 148.9, 137.1, 132.9, 132.6, 131.0, 119.9, 111.8, 111.5, 69.4, 38.0, 34.5, 31.8, 29.7, 29.4, 29.3, 29.3, 29.1, 25.3, 22.6, 14.0, 13.3

IR: 2925, 1740, 1610, 1450

EXAMPLE 68

Preparation of 2-(1-acetoxytridecyl)-5,8-dihydroxy-1,4-naphthoquinone

According to the same procedure as Example 56, except that the compound prepared in Example 48 is used as the starting compound, 387 mg of the title compound was obtained as a reddish brown precipitate.

Yield: 90%

TLC (n-hexane:ethylacetate=5:1): Rf=0.43

Melting Point: 87.5°–88.5° C.

$^1$H-NMR (CDCl$_3$, δ ppm): 12.55(s, 1H), 12.39(s, 1H), 7.16(s, 2H), 6.98(d, J=1.0 Hz, 1H), 6.00(m, 1H), 2.15(s, 3H), 1.95–1.10(m, 22H), 0.87(t, J=6.3 Hz, 3H)

$^{13}$C-NMR (CDCl$_3$, δ ppm): 178.1, 176.6, 169.8, 167.4, 166.9, 148.9, 132.8, 132.6, 131.0, 111.8, 111.5, 69.4, 34.5, 31.9, 29.6, 29.5, 29.4, 29.3, 29.1, 25.3, 22.6, 20.9, 14.0

IR: 2925, 1740, 1610, 1450

EXAMPLE 69

Preparation of 2-(1-butanoyloxytridecyl)-5,8-dihydroxy-1,4-naphthoquinone

According to the same procedure as Example 68, except that n-butanoic acid is used instead of acetic acid used in Example 68, 391 mg of the title compound was obtained as a reddish brown precipitate.

Yield: 85%

TLC (n-hexane:ethylacetate=5:1): Rf=0.50

Melting Point: 61.0°–62.0° C.

$^1$H-NMR (CDCl$_3$, δ ppm): 12.56(s, 1H), 12.40(s, 1H), 7.17(s, 1H), 6.97(d, J=0.9 Hz, 1H), 6.00(m, 1H), 2.39(t, J=7.3 Hz, 2H), 1.90–1.10(m, 24H), 0.98(t, J=6.3 Hz, 3H)

$^{13}$C-NMR (CDCl$_3$, δ ppm): 178.3, 176.7, 172.4, 167.5, 166.9, 149.2, 132.8, 132.6, 131.0, 111.8, 111.6, 69.1, 36.2, 34.6, 31.9, 29.6, 29.5(4C), 29.3, 29.1, 25.4, 22.6, 18.4, 14.0, 13.6

IR: 2925, 1740, 1610, 1450

EXAMPLE 70

Preparation of 2-(1-hexanoyloxytridecyl)-5,8-dihydroxy-1,4-naphthoquinone

According to the same procedure as Example 68, except that n-hexanoic acid is used instead of acetic acid used in Example 68, 348 mg of the title compound was obtained as a reddish brown precipitate.

Yield: 71%

TLC (n-hexane:ethylacetate=5:1): Rf=0.54

$^1$H-NMR (CDCl$_3$, δ ppm): 12.55(s, 1H), 12.39(s, 1H), 7.16(s, 2H), 6.97(d, J=0.9 Hz, 1H), 6.00(m, 1H), 2.41(t, J=7.3 Hz, 2H), 1.95–1.10(m, 28H), 1.00–0.75(m, 6H)

$^{13}$C-NMR (CDCl$_3$, δ ppm): 178.3, 176.7, 172.6, 167.4, 166.8, 149.2, 132.7, 132.6, 131.0, 111.8, 111.5, 69.1, 34.5, 34.2, 31.9, 31.2, 29.6(3C), 29.5, 29.4, 29.3, 29.1, 25.3, 24.6, 22.6, 22.3, 14.0, 13.8

IR: 2925, 1740, 1610, 1450

Preparation of the compound of formula (II)

EXAMPLE 71

Preparation of 2-(1-hydroxypentyl)-1,4,5,8-tetramethoxynaphthalene 0.8 g (33 mmole) of magnesium and 4.47 g (33 mmole) of 1-bromobutane were added to 30 ml of dry tetrahydrofuran and the mixture was stirred for 2 hours to obtain a Grignard reagent. A solution of 3 g (10.9 mmole) of 2-formyl-1,4,5,8-tetramethoxynaphthalene dissolved in 30 ml of dry tetrahydrofuran was added dropwise to the Grignard reagent over 20 minutes through a dropping funnel. The reaction mixture was stirred at normal temperature for further one hour and then 80 ml of 10% aqueous ammonium chloride solution was added thereto. The mixture was extracted twice with dichloromethane solvent, dried over anhydrous magnesium sulfate and filtered through a filter paper. The filtrate was concentrated under reduced pressure. The residue was purified by silica gel column chromatography (silica gel 4.0×20 cm) using the solvent condition which increases the amount of ethylacetate so that the n-hexane/ethylacetate ratio can vary from 10:1 to 1:1, to obtain 3.08 g of the title compound as a yellow precipitate.

Yield: 85%

TLC (n-hexane:ethylacetate=2:1): Rf=0.23

$^1$H-NMR (CDCl$_3$, δ ppm): 6.97(s, 1H), 6.80(s, 2H), 5.20(m, 1H), 3.88(s, 6H), 3.82(s, 3H), 3.72(s, 3H), 2.60(d, J=3.5 Hz, 1H), 1.76(m, 2H), 1.55–1.20(m, 4H), 0.88(t, J=6.1 Hz, 3H)

$^{13}$C-NMR (CDCl$_3$, δ ppm): 153.3, 151.3, 150.2, 146.3, 134.6, 122.5, 120.1, 108.2, 107.6, 105.8, 107.6, 105.8, 68.5, 62.7, 57.7, 57.0, 56.8, 38.0, 28.3, 22.6, 14.0

IR: 3450, 2950, 1600, 1360

MASS: 334(M$^+$, 100), 316(90), 301(27), 277(60), 262(50), 235(18), 220(15), 84(68), 57(3)

EXAMPLE 72

Preparation of 2-(1-hydroxyhexyl)-1,4,5,8-tetramethoxynaphthalene

According to the same procedure as Example 71, except that 1-bromopentane is used instead of 1-bromobutane used in Example 71, 3.1 g of the title compound was obtained as a pale yellow precipitate.

Yield: 82%

TLC (n-hexane:ethylacetate=1:1): Rf=0.42

Melting Point: 90.8°–92.0° C.

$^1$H-NMR (CDCl$_3$, δ ppm): 6.97(s, 1H), 6.80(s, 2H), 5.24(m, 1H), 3.88(s, 6H), 3.84(s, 3H), 3.73(s, 3H), 2.55(d, J=3.5 Hz, 1H), 1.76(m, 2H), 1.50–1.15(m, 4H), 0.87(t, J=6.0 Hz, 3H)

$^{13}$C-NMR (CDCl$_3$, δ ppm): 153.3, 151.3, 150.2, 146.3, 134.6, 122.5, 120.1, 108.1, 107.6, 105.8, 68.6, 62.7, 57.7, 57.0, 56.8, 38.3, 31.7, 25.8, 22.5, 14.0

IR: 3470, 2925, 1600, 1360

MASS: 348(M$^+$, 100), 277(58) 262(28) 234(21), 99 (32), 84(18)

EXAMPLE 73

Preparation of 2-(1-hydroxyoctyl)-1,4,5,8-tetramethoxynaphthalene

According to the same procedure as Example 71, except that 1-bromoheptane is used instead of 1-bromobutane used in Example 71, 3.3 g of the title compound was obtained as a yellow precipitate.

Yield: 81%

TLC (n-hexane:ethylacetate=2:1): Rf=0.24

Melting Point: 69.7°–71.2° C.

$^1$H-NMR (CDCl$_3$, δ ppm): 6.97(s, 1H), 6.79(s, 2H), 5.21(m, 1H), 3.91(s, 6H), 3.87(s, 3H), 3.72(s, 3H), 2.61(d, J=3.0 Hz, 1H), 1.75(m, 2H), 1.50–1.15(m, 10H), 0.86(t, J=6.0 Hz, 3H)

$^{13}$C-NMR (CDCl$_3$, δ ppm): 153.3, 151.3, 150.2, 146.3, 134.6, 122.5, 120.1, 108.2, 107.6, 105.9, 68.5, 62.7, 57.7, 57.0

IR: 3460, 2925, 1600, 1460

MASS: 376(M$^+$, 65), 367(20), 358(96), 344(100), 329 (19), 277(17), 246(54), 231(29), 187(6), 155(5), 127(6), 115(8), 91(7), 57(21)

EXAMPLE 74

Preparation of 2-(1-hydroxydecyl)-1,4,5,8-tetramethoxynaphthalene

According to the same procedure as Example 71, except that 1-bromononane is used instead of 1-bromobutane used in Example 71, 3.78 g of the title compound was obtained as a pale yellow precipitate.

Yield: 85%

TLC (n-hexane:ethylacetate=1:1): Rf=0.51

Melting Point: 63.0°–64.4° C.

$^1$H-NMR (CDCl$_3$, δ ppm): 6.98(s, 1H), 6.80(s, 2H), 5.24(m, 1H), 3.92(s, 6H), 3.88(s, 3H), 3.73(s, 3H), 2.54(d, J=3.4 Hz, 1H), 1.76(m, 2H), 1.55–1.10(m, 14H), 0.87(t, J=6.3 Hz, 3H)

$^{13}$C-NMR (CDCl$_3$, δ ppm): 153.3, 151.3, 150.2, 146.3, 134.6, 122.5, 120.1, 108.2, 107.6, 105.9, 68.6, 62.7, 57.7, 57.0, 56.8, 38.3, 31.8, 29.5(3C), 29.2, 26.1, 14.0

IR: 3470, 2925, 1600, 1360

MASS: 404(M$^+$, 100), 361(3), 277(77), 263(43), 235 (17), 234(16), 220(26), 85(18)

EXAMPLE 75

Preparation of 2-(1-hydroxytridecyl)-1,4,5,8-tetramethoxynaphthalene

According to the same procedure as Example 71, except that 1-bromododecane is used instead of 1-bromobutane used in Example 71, 3.55 g of the title compound was obtained as a pale yellow precipitate.

Yield: 70%

TLC (n-hexane:ethylacetate=2:1): Rf=0.30

Melting point: 69.0°–73.0° C.

$^1$H-NMR (CDCl$_3$, δ ppm): 6.97(s, 1H), 6.81(s, 2H), 5.20(br.s, 1H), 3.89(s, 3H), 3.74(m, 3H), 2.42(s, 1H), 1.76 (m, 2H), 1.50–1.00(m, 20H), 0.87(m, 3H)

$^{13}$C-NMR (CDCl$_3$, δ ppm): 153.4, 151.4, 150.2, 146.4, 134.6, 122.5, 120.1, 108.2, 107.6, 105.8, 62.8, 57.7, 57.0, 56.8, 38.3, 31.9, 29.9, 29.6, 29.3, 28.9, 28.8, 26.2, 22.6, 14.0

IR: 3440, 2920, 1600, 1460

MASS: 446(M$^+$, 100) 428(98), 413(16), 277(37), 262 (19), 233(5), 220(4), 57(2)

EXAMPLE 76

Preparation of 2-(1-acetoxy-4-methylpentyl)-1,4,5,8-tetramethoxynaphthalene

In a 25 ml two-neck flask 1 mmole of 2-(1-hydroxy-4-methylpentyl)-1,4,5,8-tetramethoxynaphthalene, 226 mg (1.1 mmole) of DCC and 30 mg (0.25 mmole) of 4-dimethylaminopyridine were introduced and then 3 ml of dry dichloromethane was added thereto. After adding 1 mmole of acetic acid at 0° C. under nitrogen gas, the reaction mixture was stirred for 30 minutes and then subsequently stirred at normal temperature for further 3 hours. To the reaction mixture was added 20 ml of n-hexane. The mixture was stirred for further 10 minutes and then filtered to remove the insoluble materials. The filtrate was dried over anhydrous magnesium sulfate to obtain a crude product. The crude product was purified by silica gel column chromatography (silica gel 2.5×20 cm) using the solvent condition which increases the amount of ethylacetate so that the n-hexane/ethylacetate ratio can vary from 20:1 to 5:1, to obtain the title compound as a pale yellow oil.

Yield: 90%

TLC (n-hexane:ethylacetate=2:1): Rf=0.59

$^1$H-NMR (CDCl$_3$, δ ppm): 6.86(s, 1H), 6.83(s, 2H), 6.33(t, J=6.3 Hz, 1H), 3.93(s, 6H), 3.89(s, 3H), 3.84(s, 3H), 2.11(s, 3H), 2.00–1.10 (m, 5H), 0.85 (d, J=6.3 Hz, 6H)

$^{13}$C-NMR (CDCl$_3$, δ ppm): 170.3, 153.4, 151.3, 150.5, 146.8, 131.1, 122.6, 120.6, 108.7, 107.7, 105.9, 71.2, 62.4, 57.9, 57.3, 56.9, 34.6, 34.0, 27.9, 22.5, 22.4, 21.2

IR: 2950, 1735, 1600, 1360

EXAMPLE 77

Preparation of 2-(1-ethoxy-4-methylpentyl)-1,4,5,8-tetramethoxynaphthalene 850 mg (2.44 mmole) of 2-(1-hydroxy-4-methylpentyl)-1,4,5,8-tetramethoxynaphthalene and 510 mg (12.2 mmole) of sodium hydride (55% dispersion in oil) were dissolved in 10 ml of dry tetrahydrofuran and 1.9 g (12.2 mmole) of iodo-ethane was added thereto under nitrogen gas and then the mixture was refluxed for 3 hours. After adding 20 ml of ice water, the reaction mixture was extracted twice with dichloromethane, dried over anhydrous magnesium sulfate and filtered through a filter paper. The filtrate was concentrated under reduced pressure to obtain a crude product. The crude product was purified by silica gel column chromatography (silica gel 2.5×15 cm) using the solvent condition which increases the amount of ethylacetate so that the n-hexane/ethylacetate ratio can vary from 10:1 to 1:1, to obtain 780 mg of the title compound as a pale yellow oil.

Yield: 85%

TLC (n-hexane:ethylacetate=2:1): Rf=0.50

$^1$H-NMR (CDCl$_3$, δ ppm): 6.98(s, 1H), 6.82(s, 2H), 4.86(m, 1H), 3.94(s, 6H), 3.89(s, 3H), 3.76(s, 3H), 3.38(q, J=7.0 Hz, 3H), 1.90–1.30(m, 5H), 1.19(t, J=7.0 Hz, 3H), 0.87(d, J=5.0 Hz, 6H)

$^{13}$C-NMR (CDCl$_3$, δ ppm): 153.5, 151.5, 150.2, 147.3, 133.4, 122.5, 120.2, 108.3, 107.6, 105.5, 75.5, 64.1, 62.5, 57.8, 56.9, 56.8, 35.7, 35.3, 28.0, 22.6, 22.5, 15.4

IR: 2950, 1600, 1450, 1360

MASS: 376(M$^+$, 12), 305(17), 276(6), 231(3), 84(100)

EXAMPLE 78

Preparation of 2-[1-(4-methylbutoxy)-4-methylpentyl]-1,4,5,8-tetramethoxynaphthalene According to the same procedure as Example 77, except that iodo-4-methylbutane is used instead of iodoethane used in Example 77, 729 mg of the title compound was obtained as a yellow oil.

Yield: 72%

TLC (n-hexane:ethylacetate=2:1): Rf=0.61

$^1$H-NMR (CDCl$_3$, δ ppm): 6.96(s, 1H), 6.82(s, 2H), 4.83(m, 1H), 3.93(s, 6H), 3.90(s, 3H), 3.75(s, 3H), 3.33(t, J=6.3 Hz, 2H), 1.90–1.10(m, 8H), 0.87(d, J=6.3 Hz, 6H), 0.83(d, J=6.3 Hz, 6H)

$^{13}$C-NMR (CDCl$_3$, δ ppm): 153.6, 151.5, 150.3, 147.3, 133.6, 122.6, 120.2, 108.3, 107.6, 105.7, 75.8, 67.4, 62.6, 57.8, 570.0(2C), 38.9, 35.3, 28.0, 25.1, 22.7, 22.6(2C), 22.5

IR: 2950, 1600, 1460, 1360

MASS: 418(M$^+$, 1), 307(3), 263(6), 237(11), 149(3), 115(3), 91(6), 71(3), 55(24), 43(100)

EXAMPLE 79

Preparation of 2-(1-pentyloxy-4-methylpentyl)-1,4,5,8-tetramethoxynaphthalene

According to the same procedure as Example 77, except that iodo-n-pentane is used instead of iodoethane used in Example 77, 850 mg of the title compound was obtained as a yellow oil.

Yield: 83%

TLC (n-hexane:ethylacetate=2:1): Rf=0.60

$^1$H-NMR (CDCl$_3$, δ ppm): 6.97(s, 1H), 6.82(s, 2H), 4.83(m, 1H), 3.94(s, 6H), 3.75(s, 3H), 3.30(t, J=6.3 Hz, 2H), 1.85–1.10(m, 11H), 0.95–0.85(m, 9H)

$^{13}$C-NMR (CDCl$_3$, δ ppm): 153.5, 151.5, 150.3, 147.3, 133.5, 122.5, 120.2, 108.3, 107.6, 105.6, 75.6, 69.0, 62.6, 57.8, 56.9(2C), 35.8, 35.3, 29.6, 28.5, 28.0, 22.6, 22.5, 22.4, 14.0

IR: 2950, 1600, 1460, 1360

EXAMPLE 80

Preparation of 2-(1-heptyloxy-4-methylpentyl)-1,4,5,8-tetramethoxynaphthalene

According to the same procedure as Example 77, except that iodo-n-heptane is used instead of iodoethane used in Example 77, 786 mg of the title compound was obtained as a yellow oil.

Yield: 72%

TLC (n-hexane:ethylacetate=2:1): Rf=0.62

$^1$H-NMR (CDCl$_3$, δ ppm): 6.98(s, 1H), 6.82(s, 2H), 4.84(m, 1H), 3.94(s, 6H), 3.76(s, 3H), 3.31(t, J=6.3 Hz, 2H), 1.90–1.10(m, 15H), 0.95–0.75(m, 9H)

$^{13}$C-NMR (CDCl$_3$, δ ppm): 153.5, 151.5, 150.2, 147.2, 133.5, 122.5, 120.2, 108.3, 107.6, 105.6, 75.6, 69.0, 62.5, 57.8, 56.9(2C), 35.8, 35.3, 31.8, 30.0, 29.6, 29.3, 28.3, 26.3, 22.6, 22.5, 22.4, 14.0

IR: 2950, 1600, 1460, 1360

EXAMPLE 81

Preparation of 2-(1-dodecyloxy-4-methylpentyl)-1,4,5,8-tetramethoxynaphthalene

According to the same procedure as Example 77, except that iodo-n-dodecane is used instead of iodoethane used in Example 77, 956 mg of the title compound was obtained as a pale yellow oil.

Yield: 76%

TLC (n-hexane:ethylacetate=2:1): Rf=0.39

$^1$H-NMR (CDCl$_3$, δ ppm): 6.96(s, 1H), 6.82(s, 2H), 4.83(m, 1H), 3.93(s, 6H), 3.89 (s, 3H), 3.75(s, 3H), 3.30(t, J=6.3 Hz, 2H), 1.90–1.10(m, 25H), 1.90–1.75(m, 9H)

$^{13}$C-NMR (CDCl$_3$, δ ppm): 153.5, 151.5, 150.3, 147.3, 133.6, 124.0, 120.2, 108.4, 107.7, 105.7, 75.5, 69.1, 62.5, 57.9, 56.9(2C), 35.8, 35.7, 35.3, 31.9, 29.9, 29.6, 29.4, 29.3, 28.0, 26.4, 22.6, 22.5, 14.0

IR: 2925, 1600, 1460, 1320

TEST 1

Experiment on Cytotoxic Activity

A. Cytotoxic activity against L1210 cells

To obtain L1210 cells in a logarithmic phase for cytotoxic activity test, in a 250 ml Erlenmeyer flask with a screw cap including Fisher medium warmed to 36° to 37° C. L1210 cells were adjusted to a concentration of 2–3×10$^5$ cells/ml and then cultured, before 24 hours from the beginning of experiment. Then, the culture solution thus obtained was suspended to prepare a L1210 cell suspension having a concentration of about 0.8–1.0×10$^6$ cells/ml. Test sample was dissoved in ethanol or dimethylsulfoxide in a certain concentration just before the experiment. 0.1 ml of the sample solution was diluted 10 times with 0.9 ml of a fresh medium. To each screw-capped test tube were added 100, 50, 25 µl, respectively, of the sample dilutions and then added 5 ml of the cell suspension (5×10$^4$ cells/ml) prepared above to use as the test group. To the test tubes for the control group (2√n: n=number of the samples), only 5 ml of the cell suspension was added. All test tubes were cultured for 48 hours in a CO$_2$ incubator at 37° C. and then the number of cells was counted using a haemacytometer.

B. Cytotoxic activity against HL-60 and K-562 cells

As in the test for the cytotoxic activity against L1210 cells, the test samples were dissoved in ethanol or dimethylsulfoxide in a certain concentration. 0.1 ml of the sample solution was mixed with 0.9 ml of a fresh medium to prepare the dilutions. To each two test tubes having a screw cap were added 100, 50, 25 µl, respectively, of the sample dilutions by means of a micropipet. To each test tube for the test group and the control group (2√n: n=number of the samples) was added 5 ml of the dilutions of HL-60 cells and K-562 cells which were cultured and activated before 24 hours from the beginning of experiment and then diluted in a concentration of 1×10$^5$ cells/mi. All test tubes were cultured for 48 hours in a CO$_2$ incubator at 37° C. and then the number of cells was counted using a haemacytometer.

The ED$_{50}$ value is defined as a concentration (µg/ml) of the sample which inhibits the growth of cancer cells by 50% of the control group and determined according to a method described in NIC's mannual (NIC=National Cancer Institue, U.S.A.). The growth rate Y(%) of cells in the presence of the test sample in each concentration was calculated according to the followign equation:

$$Y(\%) = [(T-C_o)/(C-C_o)] \times 100$$

In the above equation, T means the average cell number per ml in the test group after incubation for 48 hours in the presence of the test samples in each concentration, C means the average cell number per ml in the control group after incubation for 48 hours, and C$_o$ means the average cell number per ml in the control group at the beginning of incubation. The Y(%) value at each concentration and log$_{10}$ value of each concentration were obtained and the regression curve was constructed according to the following equation from those obtained values. In this case, when all the Y(%) value obtained at each concentration is greater than 55% or lower than 45%, the experiment was repeatedly conducted.

To construct the regression curve Y=A+BX the values A and B were obtained using the following equation.

$$B = \text{Slope} = \frac{N \cdot \Sigma(Xi \cdot Yi) - (\Sigma Xi) \cdot (\Sigma Yi)}{N \cdot \Sigma(Xi)^2 - (\Sigma Xi)^2}$$

$$A = \text{Intercept} = \frac{\Sigma Yi}{N} - B\frac{\Sigma Xi}{N}$$

In the above, the value N is the number of selected points which is greater than 2 and lower than, or identical with, the number of cencentration of the test sample, Xi is log (concentration) i, and Yi is the growth ratio at (concentration)i. The value of ED$_{50}$ was obtained for those obtained slope and intercept.

C. Cytotoxic activity against A549 cancer cells

The cytotoxic activity against A549 cancer cells was determined using a method for measuring sulforhodamin B (SRB), which was developed in the year 1989 by NIC for measuring anticancer activity of the drug in vitro. For the experiment, cells under subculturing were separated from the attached surface with trypsin-CDTA solution and then dispensed into a 24-well flat-bottom microplate (Falcon) so that the number of cells per well is 8×10$^4$ (A549). The microplate was incubated in a CO$_2$ incubator for 24 hours to attach the dispensed cells to bottom. The medium was removed with aspirator. Then, 100 µl of the solution of the test compounds diluted in a log-dose of 6 kinds of concentration was added to each well containing cells, in a multiple of 3. The microplate was incubated for further 48 hours. In addition, the diluted solution of the test compounds above was filtered through a 0.22 µm filter, before addition to the cells, to keep the experiment under sterilized condition. The cells were incubated with the test compounds for 48 hours and then the medium was removed from each well. 100 µl of 10% trichloroacetic acid (TCA) was added to each well and then the plate was allowed to stand at 4° C. for one hour to fix the cells to the bottom of plate. After fixing the cells, the plate was washed 5 to 6 times with water to completely remove any remaining TCA solution and then dried at room temperature until water is no longer present. To the completely dried plate was added the dying solution of 0.4% SRB dissolved in 1% acetic acid in an amount of 250 µl per well to stain the cells for 30 minutes and then the plate was washed again 5 to 6 times with 1% acetic acid solution to remove the remaining SRB which is not bound to the cells. The stained cell plate was dried again at room temperature. Then, the dying solution was carefully dissolved in a certain amount of 10 mM Tris so that the O.D. value in the control group at 520 nm is 0.8–1.0 Å (optical density), and the optical density at 520nm was determined. The ED$_{50}$ value was obtained from the determined optical density. To calculate the activity of the drug against cancer cells, the number of cells (Tz) at the beginning of the addition of drug, the number of cells (C) after incubation with the medium in the absence of drug for 48 hours and the number of cells (T) after incubation in the presence of drugs at each concentration for 48 hours were determined.

The anticancer activity of the test compounds was determined form the following equations. Specifically, in the case of Tz≧T the equation (T−Tz)/(C−Tz)×100 was used and in the case of Tz<T the equation (T−Tz)/Tz×100 was used. Then the IC$_{50}$ value wich is the concentration of drug which inhibits the growth of cancer cells by 50% was calcualted from the above calculated values using a data regressive function of LOTUS programme and the cytotoxic activities of the test compounds were compared with each other.

The results are listed in the following Table 1.

TABLE 1

Cytotoxic activity of the compound of the present invention against cancer cells

| Test Compounds | ED₅₀ (μg/ml) | | | |
|---|---|---|---|---|
| | L1210 | HL-60 | K562 | A549 |
| 2-(1-acetyloxy-4-methyl-3-pentenyl)-5,8-dihydroxy-1,4-naphthoquinone | <0.01 | 0.06 | | 1.0 |
| 2-(1-monochloroacetyloxy-4-methyl-3-pentenyl)-5,8-dihydroxyl-1,4-naphthoquinone | 0.12 | 0.3 | | 4.0 |
| 2-(1-trichloroacetyloxy-4-methyl-3-pentenyl)-5,8-dihydroxy-1,4-naphthoquinone | 0.01 | 0.3 | | 2.0 |
| 2-(1-n-propionyloxy-4-methyl-3-pentenyl)-5,8-dihydroxy-1,4-naphthoquinone | 0.03 | 0.04 | | 1.9 |
| 2-(1-n-butanoyloxy-4-methyl-3-pentenyl)-5,8-dihydroxy-1,4-naphthoquinone | 0.01 | 0.1 | | 2.5 |
| 2-(1-isobutanoyloxy-4-methyl-3-pentenyl)-5,8-dihydroxy-1,4-naphthoquinone | 0.003 | 0.2 | | 1.9 |
| 2-(1-n-hexanoyloxy-4-methyl-3-pentenyl)-5,8-dihydroxy-1,4-naphthoquinone | 0.2 | 0.7 | | 2.6 |
| 2-[1-(4-pentenoyl)oxy-4-methyl-3-pentenyl)-5,8-dihydroxy 1,4-naphthoquinone | 0.02 | 0.5 | | 1.0 |
| 2-[1-[3,3-dimethyl)acryloxy-4 methyl-3-pentenyl]-5,8-dihydroxy-1,4-naphthoquinone | <0.01 | 0.05 | | 1.1 |
| 2-(1-phenylacetyloxy-4-methyl-3-pentenyl)-5,8-dihydroxy-1,4-naphthoquinone | 0.1 | 0.4 | | 1.1 |
| 2-[1-(trans-2-hexenoyl)oxy-4-methyl-3-pentenyl)-5,8-dihydroxy-1,4-naphthoquinone | 0.5 | 1.0 | | 1.6 |
| 2-[1-(trans-3-hexenoyl)oxy-4-methyl-3-pentenyl-5,8-dihydroxy-1,4-naphthoquinone | 0.3 | 0.9 | | 3.3 |
| 2-[1-(6-heptenoyl)oxy-4-methyl-3-pentenyl]-5,8-dihydroxy-1,4-naphthoquinone | 0.2 | 0.5 | | 4.2 |
| 2-(1-n-octanoyloxy-4-methyl-3-pentenyl)-5,8-dihydroxy-1,4-naphthoquinone | 0.2 | 0.7 | | 4.3 |
| 2-(1-n-nonanoyloxy-4-methyl-3-pentenyl)-5,8-dihydroxy-1,4-naphthoquinone | 0.5 | 1.0 | | 6.9 |
| 2-(1-n-decanoyloxy-4-methyl-3-pentenyl)-5,8-dihydroxy-1,4-naphthoquinone | 0.7 | 1.1 | | 15 |
| 2-(1-lauryloxy-4-methyl-3-pentenyl)-5,8-dihydroxy 1,4-naphthoquinone | 0.7 | 1.0 | | >20 |
| 2-(1-diphenylacetyloxy-4-methyl-3-pentenyl)-5,8-dihydroxy-1,4-naphthoquinone | 0.2 | 0.4 | | 6.3 |
| 2-(1-undecylenoyloxy-4-methyl-3-pentenyl)-5,8-dihydroxy-1,4-naphthoquinone | 0.01 | 0.3 | | 6.7 |
| 2-(1-stearyloxy-4-methyl-3-pentenyl)-5,8-dihydroxy-1,4-naphthoquinone | 1.1 | 10 | | >20 |
| 2-(1-palmityloxy-4-methyl-3-pentenyl)-5,8-dihydroxy-1,4-naphthoquinone | 2.1 | 3.0 | | >20 |
| 2-(1-oleyloxy-4-methyl-3-pentenyl)-5,8-dihydroxy-1,4-naphthoquinone | 2.4 | 9.6 | | >20 |
| 2-(1-linolenyloxy-4-methyl-3-pentenyl)-5,8-dihydroxy-1,4-naphthoquinone | 1.5 | 4.8 | | >20 |
| 2-[1-(trans-retinoyl)oxy-4-methyl-3-pentenyl]-5,8-dihydroxy-1,4-naphthoquinone | 3.1 | 4.3 | | >20 |
| 2-[1-(cis-retinoyl)oxy-4-methyl-3-pentenyl]-5,8-dihydroxy-1,4-naphthoquinone | 7.1 | 6.6 | | >20 |
| 2-(1-pentanoyloxy-4-methyl-3-pentenyl)-5,8-dihydroxy-1,4-naphthoquinone. | 0.2 | 0.6 | | 2.5 |
| 2-[1-(trans-2-pentenoyloxy)-4-methyl-3-pentenyl-5,8-dihydroxy-1,4-naphthoquinone | 0.4 | 0.9 | | 1.1 |
| 2-[1-(2,4-hexadienoyloxy)-4-methyl-3-pentenyl]-5,8-dihydroxy-1,4-naphthoquinone | 0.5 | 0.6 | | 0.7 |
| 2-[1-(2,6-heptadienoyloxy)-4-methyl-3-pentenyl)-5,8-dihydroxy-1,4-naphthoquinone | 1.3 | 0.9 | | 3.8 |
| 2-(1-benzoyloxy-4-methyl-3-pentenyl)-5,8-dihydroxy-1,4-naphthoquinone | 0.1 | 0.1 | | 2.1 |
| 2-[1-(9,12-octadecenoyloxy)-4-methyl-3-pentenyl]-5,8-dihydroxy-1,4-naphthoquinone | 5.0 | 12.5 | | >20 |
| 2-(1-hydroxypentyl)-5,8-dimethoxy-1,4-naphthoquinone | 0.1 | 1.1 | | 6.4 |
| 2-(1-hydroxyhexyl)-5,8-dimethoxy-1,4-naphthoquinone | 0.3 | 0.6 | | 0.9 |
| 2-(1-hydroxy-4-methylpentyl)-5,8-dimethoxy-1,4-naphthoquinone | 0.02 | 0.9 | | 2.2 |
| 2-(1-hydroxyoctyl)-5,8-dimethoxy-1,4-naphthoquinone | 1.0 | 2.1 | | 7.5 |
| 2-(1-hydroxydecyl)-5,8-dimethoxy-1,4-naphthoquinone | 1.4 | 1.6 | | 9.2 |
| 2-(1-hydroxytridecyl)-5,8-dimethoxy-1,4-naphthoquinone | 1.8 | 2.3 | | 2.8 |
| 2-(1-hydroxypentyl)-5,8-dihydroxy-1,4-napthoquinone | 0.04 | 0.08 | | 0.5 |
| 2-(1-hydroxyhexyl)-5,8-dihydroxy-1,4-naphthoquinone | 0.03 | 0.02 | | 1.1 |
| 2-(1-hydroxy-4-methylpentyl)-5,8-dihydroxy-1,4-naphthoquinone | 0.05 | 0.01 | | 0.9 |
| 2-(1-hydroxyoctyl)-5,8-dihydroxy-1,4-naphthoquinone | 0.07 | 0.2 | | 0.4 |
| 2-(1-hydroxydecyl)-5,8-dihydroxy-1,4-naphthoquinone | 0.1 | 0.3 | | 0.5 |
| 2-(1-hydroxytridecyl)-5,8-dihydroxy-1,4-naphthoquinone | 0.3 | 0.4 | | 4.4 |
| 2-(1-acetoxyhexyl)-5,8-dihydroxy-1,4-naphthoquinone | 0.08 | 0.01 | | 0.7 |
| 2-(1-hexenoyloxyhexyl)-5,8-dihydroxy-1,4-naphthoquinone | 0.1 | 0.2 | | 0.3 |
| 2-(1-octanoyloxyhexyl)-5,8-dihydroxy-1,4-naphthoquinone | 0.2 | 0.3 | | 2.1 |
| 2-[1-(trans-3-hexenoyloxy)-hexyl]-5,8-dihydroxy-1,4-naphthoquinone | 0.2 | 0.2 | | 1.5 |
| 2-(1-acetoxy-4-methylpentyl)-5,8-dihydroxy-1,4-naphthoquinone | 0.05 | 0.07 | | 1.5 |
| 2-(1-hexanoyloxy-4-methylpentyl)-5,8-dihydroxy-1,4-naphthoquinone | 0.3 | 0.05 | | 0.4 |
| 2-(1-octanoyloxy-4-methylpentyl)-5,8-dihydroxy-1,4-naphthoquinone | 0.5 | 0.6 | | 1.7 |
| 2-[1-(trans-3-hexenoyloxy)-4-methylpentyl]-5,8-dihydroxy-1,4-naphthoquinone | 0.05 | 0.2 | | 2.4 |
| 2-(1-acetoxydecyl)-5,8-dihydroxy-1,4-naphthoquinone | 0.4 | 0.1 | | 0.3 |

TABLE 1-continued

Cytotoxic activity of the compound of the present invention against cancer cells

| Test Compounds | ED$_{50}$ (μg/ml) | | | |
|---|---|---|---|---|
| | L1210 | HL-60 | K562 | A549 |
| 2-(hexanoyloxydecyl)-5,8-dihydroxy-1,4-naphthoquinone | 0.5 | | 1.1 | 13.0 |
| 2-(1-octanoyloxydecyl)-5,8-dihydroxy-1,4-naphthoquinone | 0.9 | | >20 | >20 |
| 2-[1-(trans-3-hexenoyloxy)-decyl]-5,8-dihydroxy-1,4-naphthoquinone | 0.6 | | 0.6 | 7.1 |
| 2-(1-acetoxytridecyl)-5,8-dihydroxy-1,4-naphthoquinone | 0.4 | | 4.2 | 15.8 |
| 2-(1-butanoyloxytridecyl)-5,8-dihydroxy-1,4-naphthoquinone | 0.6 | | 2.7 | >20 |
| 2-(1-hexanoyloxytridecyl)-5,8-dihydroxy-1,4-naphthoquinone | 1.5 | | >20 | >20 |
| 2-(1-methoxy-4-methylpentyl)-5,8-dimethoxy-1,4-naphthoquinone | 0.2 | | 2.1 | 5.6 |
| 2-(1-ethoxy-4-methylpentyl)-5,8-dimethoxy-1,4-naphthoquinone | 0.01 | | 1.5 | 3.0 |
| 2-[1-(3-methylbutoxy)-4-methylpentyl]-5,8-dimethoxy-1,4-naphthoquinone | 2.5 | | 2.3 | 3.3 |
| 2-(1-pentyloxy-4-methylpentyl)-5,8-dimethoxy-1,4-naphthoquinone | 2.6 | | 3.0 | 7.8 |
| 2-(1-heptyloxy-4-methylpentyl)-5,8-dimethoxy-1,4-naphthoquinone | 3.1 | | 6.4 | 4.7 |
| 2-(1-dodecyloxy-4-methylpentyl)-5,8-dimethoxy-1,4-naphthoquinone | 6.3 | | 3.7 | 4.8 |
| 2-(1-methoxy-4-methylpentyl)-5,8-dihydroxy-1,4-naphthoquinone | 0.05 | | 0.07 | 1.5 |
| 2-(1-ethoxy-4-methylpentyl)-5,8-dihydroxy-1,4-naphthoquinone | 0.04 | | 0.08 | 1.7 |
| 2-[1-(3-methylbutoxy)-4-methylpentyl]-5,8-dihydroxy-1,4-naphthoquinone | 0.2 | | 0.09 | 1.1 |
| 2-(1-pentyloxy-4-methylpentyl)-5,8-dihydroxy-1,4-naphthoquinone | 0.3 | | 0.2 | 1.3 |
| 2-(1-heptyloxy-4-methylpentyl)-5,8-dihydroxy-1,4-naphthoquinone | 0.8 | | 0.2 | 2.4 |
| 2-(1-dodecyloxy-4-methylpentyl)-5,8-dihydroxy-1,4-naphthoquinone | >20 | | >20 | >20 |
| 5-Fluorouracil | 0.02 | 0.2 | 1.0 | 3.7 |

As can be seen from the above result, it is apparant that the novel 5,8-dihydroxy-1,4-naphthoquinone derivative of formula (IA) of the present invention shows a cytotoxic activity similar to, or superior to, the currently, widely-used anticancer agent, Fluorouracil, and therefore can be used as a clinically useful anticancer agent.

TEST 2

Animal Experiment Using Sarcoma S-180 Cells

In this experiment, healthy male ICR mouse weighing 20 to 25 g were used as test animal and were fed with water and feed without any restriction in the chamber controlled at the temperature of 23° to 24° C. As the feed, the antibiotic-free feed for mouse was used.

S-180 cells which were incubated for 7 days within abdominal cavity of ICR mouse were separated together with ascites. To the separated cells was added sterilized cold physiological saline and the mixture was centrifuged with 400×g for 2 minutes to separate the cell precipitate. The separated cell precipitate was suspended again in sterilized cold physiological saline and then centrifuged to remove the supernatant. Only S-180 cells were taken, excluding any red bllod cells incorporated therein, washed three times with the same method as above, and then suspended to obtain the cell suspension in concentration of $10^7$ cells/ml by counting the number of cells with a haemacytometer. Each 0.1 ml of this cell suspension was transplanted in an abdominal cavity.

After 24 hours from the transplantation, mouse were divided so that each group contains 8 to 9 mouse. The test sample was dissolved in a predetermined amount of dimethylsulfoxide to prepare the stock solution which was stored at 4° C. 30 μl of the stock solution was taken and then mixed with 1.5 ml of physiological saline. 0.1 ml of this mixture was intraperitoneally injected to the test animal. To the control group, 2% dimethylsulfoxide-physiological saline solution was injected. Meanwhile, doxorubicin which is used as the comparative drug was dissolved in 2% dimethylsulfoxide-physiological saline solution and then injected in an amount of 0.5 mg(titer)/kg. The schedule for injection comprises a total of 7 to 8 injections in the manner that after the transplantation of cancer cells 0.1 ml of the test sample per a day is administered for 2 to 4 days followed by the rest for one day. The survival rate was calculated on the basis of the date on which all of one control group is died (approximately 18 to 20 days). The survival rate (T/C, %) was calculated by the following equation as proposed in NIC's protocol:

$$\text{Survival rate } (T/C, \%) = \frac{\text{Average survived period in the test group}}{\text{Average survived period in the control group}} \times 100$$

The results as obatined above are described in the following Table 2.

TABLE 2

Anticancer activity of the compound of the present invention against S-180 sarcoma cells

| Test compounds | Dose mg/kg/day (μmole) | T/C (%) | Number of mouse survived for 50 days |
|---|---|---|---|
| 2-(1-acetyloxy-4-methyl-3-pentenyl)-5,8-dihydroxy-1,4-naphthoquinone | 1.65 (5) | 160 | 0/8 |
| 2-(1-monochloroacetyloxy-4-methyl-3-pentenyl)-5,8-dihydroxy-1,4-naphthoquinone | 3.64 (10) | 102 | 0/8 |
| 2-(1-trichloroacetyloxy-4-methyl-3-pentenyl)-5,8-dihydroxy-1,4-naphthoquinone | 4.33 (10) | 134 | 0/8 |
| 2-(1-n-propionyloxy-4-methyl-3-pentenyl)-5,8-dihydroxy-1,4-naphthoquinone | 1.72 (5) | 100 | 0/8 |
| 2-(1-n-butanoyloxy-4-methyl-3-pentenyl)-5,8-dihydroxy-1,4-naphthoquinone | 3.58 (10) | 181 | 0/8 |
| 2-(1-isobutanoyloxy-4-methyl-3-pentenyl)-5,8-dihydroxy-1,4-naphthoquinone | 3.58 (10) | 185 | 1/8 |
| 2-(1-n-hexanoyloxy-4-methyl-3-pentenyl)-5,8-dihydroxy-1,4-naphthoquinone | 3.86 (10) | 214 | 3/9 |
| 2-[1-(4-pentenoyl)oxy-4-methyl-3-pentenyl]-5,8-dihydroxy- | 3.70 (10) | 180 | 1/7 |

TABLE 2-continued

Anticancer activity of the compound of the present invention against S-180 sarcoma cells

| Test compounds | Dose mg/kg/day (μmole) | T/C (%) | Number of mouse survived for 50 days |
|---|---|---|---|
| 1,4-naphthoquinone | | | |
| 2-[1-(3,3-dimethyl)acryloxy-4-methyl-3-pentenyl]-5,8-dihydroxy-1,4-naphthoquinone | 3.70 (10) | 179 | 2/8 |
| 2-(1-phenylacetyloxy-4-methyl-3-pentenyl)-5,8-dihydroxy-1,4-naphthoquinone | 4.06 (10) | 183 | 0/8 |
| 2-[1-(trans-2-hexenoyl)oxy-4-methyl-3-pentenyl]-5,8-dihydroxy-1,4-naphthoquinone | 3.84 (10) | 160 | 1/8 |
| 2-[1-(trans-3-hexenoyl)oxy-4-methyl-3-pentenyl]-5,8-dihydroxy-1,4-naphthoquinone | 3.84 (10) | 200 | 2/8 |
| 2-[1-(6-heptenoyl)oxy-4-methyl-3-pentenyl]-5,8-dihydroxy-1,4-naphthoquinone | 3.98 (10) | 192 | 1/8 |
| 2-(1-n-octanoyloxy-4-methyl-3-pentenyl)-5,8-dihydroxy-1,4-naphthoquinone | 6.27 (15) | 235 | 2/9 |
| 2-(1-n-nonanoyloxy-4-methyl-3-pentenyl)-5,8-dihydroxy-1,4-naphthoquinone | 4.28 (10) | 206 | 0/8 |
| 2-(1-n-decanoyloxy-4-methyl-3-pentenyl)-5,8-dihydroxy-1,4-naphthoquinone | 6.72 (15) | 110 | 0/9 |
| 2-(1-lauryloxy-4-methyl-3-pentenyl)-5,8-dihydroxy-1,4-napthoquinone | 7.14 (15) | 110 | 0/9 |
| 2-(1-diphenylacetyloxy-4-methyl-3-pentenyl)-5,8-dihydroxy-1,4-naphthoquinone | 7.23 (15) | 208 | 2/8 |
| 2-(1-undecylenoyloxy-4-methyl-3-pentenyl)-5,8-dihydroxy-1,4-naphthoquinone | 6.81 (15) | 110 | 0/8 |
| 2-(1-stearyloxy-4-methyl-3-(pentenyl)-5,8-dihydroxy-1,4-naphthoquinone | 8.31 (15) | 110 | 0/9 |
| 2-(1-palmityloxy-4-methyl-3-pentenyl)-5,8-dihydroxy-1,4-naphthoquinone | 7.89 (15) | 109 | 0/9 |
| 2-(1-oleyloxy-4-methyl-3-pentenyl)-5,8-dihydroxy-1,4-naphthoquinone | 8.28 (15) | 130 | 0/9 |
| 2-(1-linolenyloxy-4-methyl-3-pentenyl)-5,8-dihydroxy-1,4-naphthoquinone | 8.22 (15) | 125 | 0/9 |
| 2-[1-(trans-retinoyl)oxy-4-methyl-3-pentenyl]-5,8-dihydroxy-1,4-naphthoquinone | 17.3 (15) | 107 | 0/8 |
| 2-[1-(cis-retinoyl)oxy-4-methyl-3-pentenyl]-5,8-dihydroxy-1,4-naphthoquinone | 17.3 (15) | 125 | 0/9 |
| 2-(1-pentanoyloxy-4-methyl-3-pentenyl)-5,6-dihydroxy-1,4-naphthoquinone | 3.72 (10) | 165 | 0/8 |
| 2-[1-(trans-2-pentenyloxy)-4-methyl-3-pentenyl]-5,8-dihydroxy-1,4-naphthoquinone | 5.61 (15) | 210 | 1/7 |
| 2-[1-(2,4-hexadienoyloxy)-4-methyl-3-pentenyl]-5,8-dihydroxy-1,4-naphthoquinone | 3.82 (10) | 185 | 2/8 |
| 2-[1-(2,6-heptadienoyloxy)-4-methyl-3-pentenyl]-5,8-dihydroxy-1,4-naphthoquinone | 3.96 (10) | 180 | 1/8 |
| 2-(1-benzoyloxy-4-methyl-3-pentenyl)-5,8-dihydroxy-1,4-naphthoquinone | 3.92 (10) | 135 | 0/8 |
| 2-[1-(9,12-octadecenyloxy)-4-methyl-3-pentenyl]-5,8-dihydroxy-1,4-naphthoquinone | 8.25 (15) | 100 | 0/8 |
| 2-(1-hydroxy-4-methylpentyl)-5,8-dimethoxy-1,4-naphthoquinone | 3.18 (10) | 120 | 0/8 |
| 2-(1-hydroxy-4-methylpentyl)-5,8-dihydroxy-1,4-naphthoquinone | 1.95 (5) | 120 | 0/8 |
| 2-(1-hydroxytridecyl)-5,8-dihydroxy-1,4-naphthoquinone | 3.38 (10) | 113 | 0/8 |
| 2-(1-acetoxyhexyl)-5,8-dihydroxy-1,4-naphthoquinone | 1.66 (5) | 150 | 2/8 |
| 2-(1-hexanoyloxyhexyl)-5,8-dihydroxy-1,4-naphthoquinone | 3.88 (10) | 151 | 0/7 |
| 2-(1-octanoyloxyhexyl)-5,8-dihydroxy-1,4-naphthoquinone | 6.24 (15) | 95 | 0/8 |
| 2-[1-(trans-3-hexenoyloxy)-hexyl]-5,8-dihydroxy-1,4-naphthoquinone | 3.86 (10) | 105 | 0/7 |
| 2-(1-acetoxy-4-methylpentyl)-5,8-dihydroxy-1,4-naphthoquinone | 1.66 (5) | 188 | 1/7 |
| 2-(1-hexanoyloxy-4-methylpentyl)-5,8-dihydroxy-1,4-naphthoquinone | 3.88 (10) | 151 | 0/8 |
| 2-(1-octanoyloxy-4-methylpentyl)-5,8-dihydroxy-1,4-naphthoquinone | 6.24 (15) | 131 | 0/8 |
| 2-[1-(trans-3-hexenoyloxy)-4-methylpentyl]-5,8-dihydroxy-1,4-naphthoquinone | 3.86 (10) | 160 | 0/7 |
| 2-(1-acetoxydecyl)-5,8-dihydroxy-1,4-naphthoquinone | 3.88 (10) | 197 | 1/7 |
| 2-[1-(trans-3-hexenoyloxy)-decyl]-5,8-dihydroxy-1,4-naphthoquinone | 4.42 (10) | 130 | 0/7 |
| 2-(1-acetoxytridecyl)-5,8-dihydroxy-1,4-naphthoquinone | 4.30 (10) | 131 | 1/7 |
| 2-(1-ethoxy-4-methylpentyl)-5,8-dihydroxy-1,4-naphthoquinone | 3.46 (10) | 105 | 0/8 |
| 2-(1-methoxy-4-methylpentyl)-5,8-dihydroxy-1,4-naphthoquinone | 3.04 (10) | 126 | 0/8 |
| 2-[1-(3-methylbutoxy)-4-methylpentyl]-5,8-dihydroxy-1,4-naphthoquinone | 5.49 (15) | 186 | 0/7 |
| Doxorubicin | 0.5 (1.2) | 230 | 4/9 |

As can be seen from the above result, it is apparant that the compound of the present invention shows a potent cytotoxic activity against cancer cells and further exhibits an excellent LSI effect similar to, or superior to, the currently, widely-used anticancer agent, Doxorubicin, in mouse suffering from S-180 sarcoma, and therefore can be used as a clinically useful anticancer agent.

What is claimed is:

1. A process for preparing 5,8-dihydroxynaphthoquinone derivatives represented by the following general formula (I):

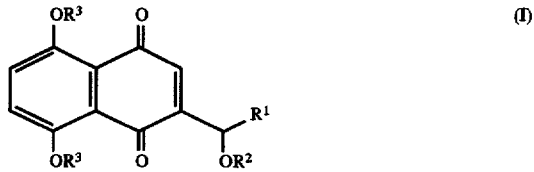

in which $R^1$ represents alkyl or alkenyl, $R^2$ represents hydrogen, alkyl or a group —C(O)R wherein R represents alkyl, alkenyl, aryl, aralkyl or arakenyl, which can be substituted or unsubstituted with one or more halogen(s), and $R^3$ represents hydrogen or alkyl, characterized in that (B) a compound having the following general formula (Ia):

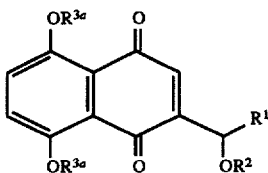

(Ia)

wherein $R^1$ and $R^2$ are defined as previously described and $R^{3a}$ represents alkyl, is dealkylated in the presence of boron tribromide, HCl pyridine, aluminum chloride or silver oxide-nitric acid compound to prepare a compound having the following general formula (Ib):

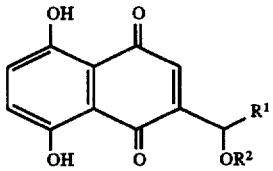

(Ib)

wherein $R^1$ and $R^2$ are defined as previously described.

2. The process as defined in claim 1, characterized in that silver oxide-nitric acid compound is used as the dealkylating agent.

3. A process for preparing 5,8-dihydroxynaphthoquinone derivatives represented by the following general formula (I):

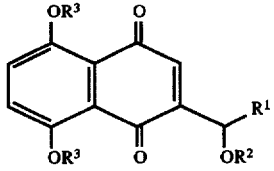

(I)

in which $R^1$ represents alkyl or alkenyl, $R^2$ represents hydrogen, alkyl or a group —C(O)R wherein R represents alkyl, alkenyl, aryl, aralkyl or arakenyl, which can be substituted or unsubstituted with one or more halogen(s), and $R^3$ represents hydrogen or alkyl, characterized in that (C) a compound having the following general formula (Ic):

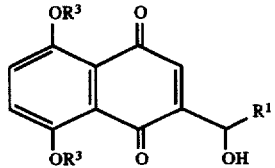

(Ic)

wherein $R^1$ and $R^3$ are defined as previously described, is reacted with a compound of formula RCOOH wherein R is defined as previously described, in the presence of an organic base and dicyclohexylcarbodiimide to prepare a compound having the following general formula (Id):

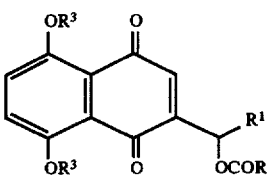

(Id)

wherein $R^1$, $R^3$ and R are defined as previously described.

4. The process as defined in claim 3, characterized in that in the method (C) the reaction solvent is an optionally chlorinated hydrocarbon solvent.

5. The process as defined in claim 3, characterized in that in the method (C) 1.0 to 2.0 mole of dicyclohexylcarbodiimide and 0.01 to 0.5 mole of the organic base are used with respect to 1 mole of the compound of formula (Ic).

6. A novel 5,8-dihydroxynaphthoquinone derivative represented by the following general formula (IA):

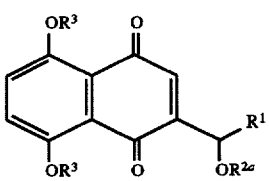

(IA)

in which $R^1$ represents alkyl or alkenyl, $R^{2a}$ represents alkyl or a group —C(O)R wherein R represents alkyl, alkenyl, aryl, aralkyl or aralkenyl, which can be substituted or unsubstituted with one or more halogen(s), and $R^3$ represents hydrogen or alkyl, provided that when $R^{2a}$ is a group —C(O)R and $R^3$ is hydrogen, $R^1$ is other than 3-methyl-2-butenyl; and when $R^{2a}$ represents methyl and $R^3$ independently represents hydrogen or methyl, $R^1$ is other than 3-methylbutyl.

7. The 5,8-dihydroxynaphthoquinone derivative of formula (I) as defined in claim 6, wherein $R^1$ represents $C_1-C_{15}$ alkyl or $C_2-C_{15}$ alkenyl, $R^{2a}$ represents $C_1-C_{15}$ alkyl or a group —C(O)R wherein R represents $C_1-C_{15}$ alkyl, $C_2-C_{15}$ alkenyl, phenyl, phenyl-$C_1-C_{15}$ alkyl or phenyl-$C_2-C_{15}$ alkenyl, which can be substituted or unsubstituted with one or more chlorine atom(s), and $R^3$ represents hydrogen or $C_1-C_{15}$ alkyl, provided that when $R^{2a}$ is a group —C(O)R and $R^3$ is hydrogen, $R^1$ is other than 3-methyl-2-butenyl; and when $R^{2a}$ represents methyl and $R^3$ independently represents hydrogen or methyl, $R^1$ is other than 3-methylbutyl.

8. An anticancer composition containing the 5,8-dihydroxynaphthoquinone derivative of formula (IA) according to claims 6 as an active ingredient.

* * * * *